(12) United States Patent
Beadle et al.

(10) Patent No.: US 12,419,790 B2
(45) Date of Patent: Sep. 23, 2025

(54) APPARATUSES AND METHODS FOR NEGATIVE PRESSURE WOUND THERAPY

(71) Applicant: T.J.Smith and Nephew, Limited, Hull (GB)

(72) Inventors: Victoria Beadle, Hull (GB); Varuni Rachindra Brownhill, Swanland (GB); Brian Gilchrist, Loosley Row (GB); Danielle Susan Johnson, Hull (GB); Luke Michael Parry, Goole (GB); Hannah Bailey Weedon, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 346 days.

(21) Appl. No.: 17/921,597

(22) PCT Filed: Apr. 28, 2021

(86) PCT No.: PCT/EP2021/061186
§ 371 (c)(1),
(2) Date: Oct. 26, 2022

(87) PCT Pub. No.: WO2021/219752
PCT Pub. Date: Nov. 4, 2021

(65) Prior Publication Data
US 2023/0165724 A1 Jun. 1, 2023

(30) Foreign Application Priority Data

Apr. 29, 2020 (GB) ..................... 2006305

(51) Int. Cl.
*A61F 13/05* (2024.01)
*A61F 13/0203* (2024.01)
(Continued)

(52) U.S. Cl.
CPC .......... *A61F 13/05* (2024.01); *A61F 13/0203* (2013.01); *A61M 1/90* (2021.05); *A61F 2013/00089* (2013.01)

(58) Field of Classification Search
CPC ......... A61M 1/90; A61M 1/917; A61F 13/05; A61H 9/0057; A61H 9/0092
See application file for complete search history.

(56) References Cited

U.S. PATENT DOCUMENTS 3,903,882 A 9/1975 Augurt
4,181,127 A 1/1980 Linsky et al.
(Continued)

FOREIGN PATENT DOCUMENTS

DE 102008020553 A1 10/2008
EP 0507459 A1 10/1992
(Continued)

OTHER PUBLICATIONS

International Search Report and Written Opinion for Application No. PCT/EP2021/061186, mailed on Aug. 24, 2021, 14 pages.
(Continued)

*Primary Examiner* — Keri J Nelson
(74) *Attorney, Agent, or Firm* — Knobbe, Martens, Olson & Bear, LLP

(57) ABSTRACT

Disclosed embodiments related to a wound dressing for treating circumferential wounds for use in a negative pressure wound therapy (NPWT). The wound dressing can include a cover layer, a plurality of spacer sections, and a wound contact layer. The wound dressing can further include a port for connection to a source of negative pressure and a connector for fluidically connecting each of the plurality of sections with the port.

17 Claims, 21 Drawing Sheets

(51) Int. Cl.
*A61M 1/00* (2006.01)
*A61F 13/00* (2006.01)

(56) References Cited

U.S. PATENT DOCUMENTS

| | | | |
|---|---|---|---|
| 5,308,313 | A | 5/1994 | Karami et al. |
| 5,540,922 | A | 7/1996 | Fabo |
| 5,549,584 | A | 8/1996 | Gross |
| 5,636,643 | A | 6/1997 | Argenta et al. |
| 6,653,520 | B1 | 11/2003 | Mouton |
| 7,338,482 | B2 | 3/2008 | Lockwood et al. |
| 7,569,742 | B2 | 8/2009 | Haggstrom et al. |
| 7,708,724 | B2 | 5/2010 | Weston |
| 7,723,560 | B2 | 5/2010 | Lockwood et al. |
| 7,779,625 | B2 | 8/2010 | Joshi et al. |
| 7,909,805 | B2 | 3/2011 | Weston |
| 7,959,624 | B2 | 6/2011 | Riesinger |
| 7,985,209 | B2 | 7/2011 | Villanueva et al. |
| 8,062,272 | B2 | 11/2011 | Weston |
| 8,172,816 | B2 | 5/2012 | Kazala, Jr. et al. |
| 8,513,481 | B2 | 8/2013 | Gergely et al. |
| 8,679,080 | B2 | 3/2014 | Kazala, Jr. et al. |
| 8,708,998 | B2 | 4/2014 | Weston et al. |
| 8,801,685 | B2 | 8/2014 | Armstrong et al. |
| 8,808,274 | B2 | 8/2014 | Hartwell |
| 10,080,689 | B2 | 9/2018 | Hall et al. |
| 10,548,777 | B2 | 2/2020 | Locke et al. |
| 10,940,046 | B2 | 3/2021 | Locke |
| 11,007,084 | B2 | 5/2021 | Robinson et al. |
| 11,224,543 | B2 | 1/2022 | Locke |
| 11,614,170 | B2 | 3/2023 | Tumey et al. |
| 11,752,252 | B2 | 9/2023 | Randolph et al. |
| 12,178,954 | B2 | 12/2024 | Robinson et al. |
| 2003/0045825 | A1 | 3/2003 | Etheredge, III |
| 2003/0153860 | A1 | 8/2003 | Nielsen et al. |
| 2003/0212359 | A1 | 11/2003 | Butler |
| 2004/0127836 | A1 | 7/2004 | Sigurjonsson et al. |
| 2004/0138602 | A1 | 7/2004 | Rossen |
| 2004/0200094 | A1 | 10/2004 | Baychar |
| 2006/0241542 | A1 | 10/2006 | Gudnason et al. |
| 2006/0282028 | A1 | 12/2006 | Howard et al. |
| 2008/0167593 | A1 | 7/2008 | Fleischmann |
| 2009/0234307 | A1 | 9/2009 | Vitaris |
| 2009/0299251 | A1 | 12/2009 | Buan |
| 2010/0010462 | A1 | 1/2010 | Kurata |
| 2011/0004172 | A1 | 1/2011 | Eckstein et al. |
| 2011/0112492 | A1 | 5/2011 | Bharti et al. |
| 2011/0224631 | A1 | 9/2011 | Simmons et al. |
| 2012/0238932 | A1 | 9/2012 | Atteia et al. |
| 2012/0253302 | A1 | 10/2012 | Corley |
| 2015/0190286 | A1 | 7/2015 | Allen et al. |
| 2016/0135998 | A1 | 5/2016 | Riesinger |
| 2017/0291020 | A1 | 10/2017 | Tolia et al. |
| 2018/0021178 | A1 | 1/2018 | Locke et al. |
| 2018/0228945 | A1 | 8/2018 | Guirguis et al. |
| 2018/0333522 | A1* | 11/2018 | Pratt .................. A61F 13/148 |
| 2018/0353336 | A1 | 12/2018 | Locke et al. |
| 2018/0353338 | A1 | 12/2018 | Locke et al. |
| 2018/0353662 | A1 | 12/2018 | Locke et al. |
| 2018/0353663 | A1 | 12/2018 | Locke et al. |
| 2018/0369462 | A1 | 12/2018 | Anderson et al. |
| 2019/0015258 | A1 | 1/2019 | Gowans et al. |
| 2019/0029886 | A1 | 1/2019 | Lin |
| 2019/0110932 | A1 | 4/2019 | Mumby et al. |
| 2019/0117861 | A1 | 4/2019 | Locke et al. |
| 2019/0192350 | A1 | 6/2019 | Gowans et al. |
| 2019/0307935 | A1 | 10/2019 | Simmons et al. |
| 2020/0038283 | A1* | 2/2020 | Hall .................. A61H 7/001 |
| 2020/0069477 | A1 | 3/2020 | Holm et al. |
| 2020/0093646 | A1 | 3/2020 | Locke et al. |
| 2020/0107965 | A1 | 4/2020 | Greener |
| 2020/0170841 | A1 | 6/2020 | Waite et al. |
| 2020/0214897 | A1 | 7/2020 | Long et al. |
| 2020/0246190 | A1 | 8/2020 | Luckemeyer et al. |
| 2020/0268561 | A1 | 8/2020 | Locke et al. |
| 2020/0297905 | A1 | 9/2020 | Gellman et al. |
| 2020/0306092 | A1 | 10/2020 | Rehbein et al. |
| 2020/0306430 | A1 | 10/2020 | Rehbein et al. |
| 2021/0106737 | A1 | 4/2021 | Obst et al. |
| 2021/0128340 | A1 | 5/2021 | Jahanian et al. |
| 2021/0161725 | A1 | 6/2021 | Edwards et al. |
| 2021/0177661 | A1 | 6/2021 | Poole et al. |
| 2022/0117797 | A1 | 4/2022 | Adie et al. |
| 2022/0152287 | A1 | 5/2022 | Loske |
| 2022/0184294 | A1 | 6/2022 | Locke et al. |
| 2023/0201445 | A1 | 6/2023 | Earl et al. |
| 2024/0074910 | A1 | 3/2024 | Askem et al. |
| 2024/0074911 | A1 | 3/2024 | Madriz et al. |
| 2024/0390191 | A1 | 11/2024 | Jeyakumaran et al. |

FOREIGN PATENT DOCUMENTS

| | | |
|---|---|---|
| EP | 3023083 A1 | 5/2016 |
| EP | 3365039 B1 | 11/2020 |
| GB | 2527617 A | 12/2015 |
| JP | S61288860 A | 12/1986 |
| JP | 2004521665 A | 7/2004 |
| JP | 2012024124 A | 2/2012 |
| JP | 2014065183 A | 4/2014 |
| WO | WO-2007082538 A1 | 7/2007 |
| WO | WO-2009066106 A1 | 5/2009 |
| WO | WO-2011063818 A1 | 6/2011 |
| WO | WO-2013175306 A2 | 11/2013 |
| WO | WO-2014003957 A1 | 1/2014 |
| WO | WO-2014140606 A1 | 9/2014 |
| WO | WO-2014140608 A1 | 9/2014 |
| WO | WO-2015052219 A1 | 4/2015 |
| WO | WO-2015193257 A1 | 12/2015 |
| WO | WO-2016018706 A1 | 2/2016 |
| WO | WO-2016174048 A1 | 11/2016 |
| WO | WO-2017186771 A1 | 11/2017 |
| WO | WO-2018125739 A1 | 7/2018 |
| WO | WO-2018226630 A1 | 12/2018 |
| WO | WO-2018226667 A1 | 12/2018 |
| WO | WO-2019027731 A1 | 2/2019 |
| WO | WO-2019067264 A1 | 4/2019 |
| WO | WO-2019083868 A1 | 5/2019 |
| WO | WO-2019226900 A1 | 11/2019 |
| WO | WO-2020005535 A1 | 1/2020 |
| WO | WO-2020046935 A1 | 3/2020 |
| WO | WO-2021001737 A1 | 1/2021 |
| WO | WO-2021009712 A1 | 1/2021 |
| WO | WO-2021014297 A1 | 1/2021 |
| WO | WO-2021033051 A1 | 2/2021 |
| WO | WO-2021033052 A1 | 2/2021 |
| WO | WO-2021059124 A1 | 4/2021 |
| WO | WO-2021116977 A1 | 6/2021 |

OTHER PUBLICATIONS

Smith & Nephew, "Allevyn: Technical Information Sheet," Dec. 2013, 2 pages.
International Preliminary Report on Patentability for Application No. PCT/EP2021/061186, mailed on Nov. 10, 2022, 8 pages.

* cited by examiner

APPARATUSES AND METHODS FOR NEGATIVE PRESSURE WOUND THERAPY

CROSS-REFERENCE TO RELATED APPLICATIONS

This application is a U.S. national stage application of International Patent Application No. PCT/EP2021/061186, filed Apr. 28, 2021 and now Publication No. WO 2021/219752, which claims priority to U.K. Provisional Application No. 2006305.3 filed on Apr. 29, 2020; the disclosures of which are hereby incorporated by reference in their entirety.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy (NPWT), or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

Venous leg ulcers often fall into the category of difficult-to-heal wounds, therefore treatment can be time-consuming and costly, affecting patients' quality of life. Venous leg ulcers are often treated with compression bandages in attempt to reduce oedema and improve vein circulation. The pressure applied via compression bandage dressing (P) can be modeled via the below equation.

$$P = \frac{T \times N \times (\text{constant})}{C \times W}$$

In this equation, T stands for the tension of the bandage (Kgf), N stands for the number of layers, C stands for the circumference at the measurement point, and W stands for the width of the bandage. Therefore, the pressure applied via the compression bandage is inversely proportional to the circumference at the point of pressure, and thus the pressure applied to the leg would vary along various locations with different circumferences. For example, when compression bandage dressings start at the toes and work up to the patient's leg to their knees, the pressure applied via the compression bandage dressing is different at the toe from at the calf. Accordingly, an alternative to compression bandage which can apply constant pressure to the leg may be needed. Also, it has been reported that compression bandaging is often not applied correctly and can cause pain to the patient, resulting in delayed wound healing or even tissue necrosis.

As an alternative to compression bandages, TNP therapy may be used to apply constant compression forces to the treatment area and provide prolonged exudate removal. Accordingly, a wound dressing for TNP therapy of circumferential wounds, such venous leg ulcers, is desired.

SUMMARY

Embodiments of the invention disclosed herein are directed to apparatuses, systems, devices and methods for use in negative pressure wound therapy.

In some configurations, a negative pressure wound therapy dressing configured for treating a circumferential surface includes a cover layer, a wound contact layer, a plurality of spacer sections positioned between the cover layer and the wound contact layer, a port configured to be connected to a source of negative pressure; and a connector configured to fluidically connect each of the plurality of spacer sections with the port. Each spacer section is separated from another section by a gap region therebetween. The cover layer and the wound contact layer are configured to be sealed together at the one or more gap regions.

The negative pressure wound therapy dressing of the preceding paragraph can include one or more of the following features. The connector can include a plurality of inlets connected to the plurality of spacer sections and an outlet connected to the port. The connector can include a spacer fabric material. Each of the spacer sections can include a distal end, a proximal end, a length extending from the distal end to the proximal end, and a width perpendicular to the length. The connector can be connected to the proximal end of a spacer section. The length can be greater than the width. Each of the spacer sections can be fluidically isolated from the other spacer sections except for at the connector. The dressing can be trimmable. The dressing can further include one or more tubes connecting the plurality of spacer sections and the connector. The cover layer can include one or more openings and the port can be positioned above the one or more openings. The cover layer can include an extension portion at one end of the cover layer, wherein the extension portion can be overlapped over another regions of the cover layer when the dressing is applied to a wound.

In some configurations, a method of treating a circumferential wound can include providing a wound dressing and applying the wound dressing around the circumferential wound. The wound dressing includes a cover layer, a wound contact layer, a plurality of spacer sections positioned between the cover layer and the wound contact layer, a port configured to be connected to a source of negative pressure, and a connector configured to fluidically connect each of the plurality of sections with the port. Each spacer section is separated from another section by a gap region therebetween. The cover layer and the wound contact layer are configured to be sealed together at the one or more gap regions.

The method of treating a circumferential wound of the preceding paragraph can include one or more of the following features. Applying the wound dressing around the circumferential wound can include wrapping the wound dressing around the circumferential wound such that an end of the cover layer overlaps with the other end of the cover layer. The cover layer can include an extension portion at one end of the cover layer, wherein the extension portion can be overlapped over another regions of the cover layer. The method can further include applying negative pressure to the circumferential wound through the port. The method can further include trimming a portion of the wound dressing. The method can further include trimming a portion of the wound dressing along a trim line along the gap region and across the connector. The connector can further include a plurality of inlets connected to the plurality of spacer sections and an outlet connected to the port. The connector can further include a spacer fabric material. Each of the spacer sections can include a distal end, a proximal end, a length extending from the distal end to the proximal end, and a width perpendicular to the length, wherein applying the wound dressing around the circumferential wound can include positioning the length of the spacer sections along the length of the circumferential wound. The connector can be connected to the proximal end of a spacer section. The length can be greater than the width. Each of the spacer sections can be fluidically isolated from the other spacer sections except for at the connector. The wound dressing can further include one or more tubes connecting the plurality of spacer sections and the connector. The cover layer can include one or more openings and the port can be positioned above the one or more openings.

Alternative or additional embodiments described herein provide an apparatus to provide negative pressure to a wound site comprising one or more of the features of the foregoing description or of any description elsewhere herein.

Alternative or additional embodiments described herein provide a method of operating a negative pressure wound therapy apparatus comprising one or more of the features of the foregoing description or of any description elsewhere herein.

Alternative or additional embodiments described herein provide a method of treating a wound comprising one or more of the features of the foregoing description or of any description elsewhere herein.

DETAILED DESCRIPTION

Overview

Embodiments disclosed herein relate to apparatuses, systems, devices and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760−X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
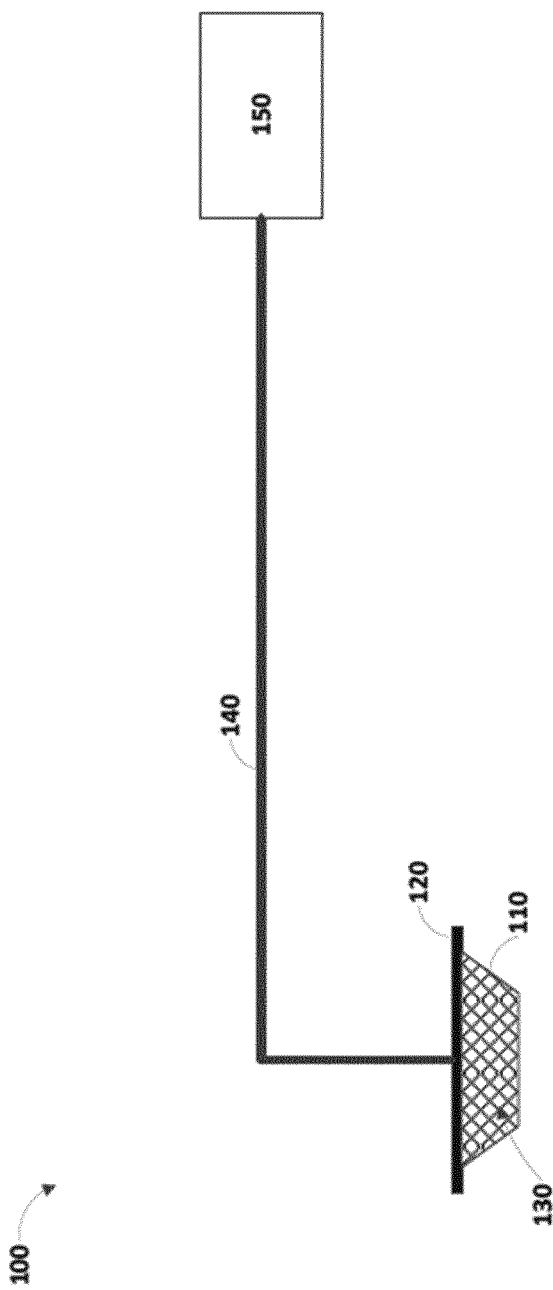
FIG. 1 illustrates a reduced pressure wound therapy system according to some embodiments.

FIG. 1 illustrates an embodiment of a negative or reduced pressure wound treatment (or TNP) system 100 including a wound filler 130 placed inside a wound cavity 110, the wound cavity sealed by a wound cover 120. The wound filler 130 in combination with the wound cover 120 can be referred to as wound dressing. A flow path 140, such as a single or multi lumen tube or conduit, is connected to the wound cover 120 with a negative pressure wound therapy device, for example pump assembly 150, configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110. The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg. Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150. In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −125 mmHg, −140 mmHg, −160 mmHg, −180 mmHg, −200 mmHg, or below −200 mmHg. During intermittent therapy, negative pressure at low setpoint can be delivered for a first-time duration, and upon expiration of the first-time duration, negative pressure at high setpoint can be delivered for a second-time duration. Upon expiration of the second-time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like. The negative pressure delivered during intermittent therapy can be pulsating or cause pulsation on the limb or other body or tissue location.

In some embodiments, the TNP system 100 can include multiple wound dressings connected to the pump assembly 150. The performance and wound healing capabilities (such as, fluid management) of the TNP system with multiple wound dressings with the pump assembly 150 can be equivalent to or exceed that of a standard single wound dressing with single pump set-up.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Any of the dressings described herein can be used with Smith and Nephew's Renasys Soft Port connector or interface between the dressing and the pump assembly. For example, the Renasys Soft Port connector can be positioned in the flow path 140 and serve as a port for the wound dressing. In other embodiments, other suitable wound dressings can be utilized.

Pump Assembly and Canister

Figure 2:
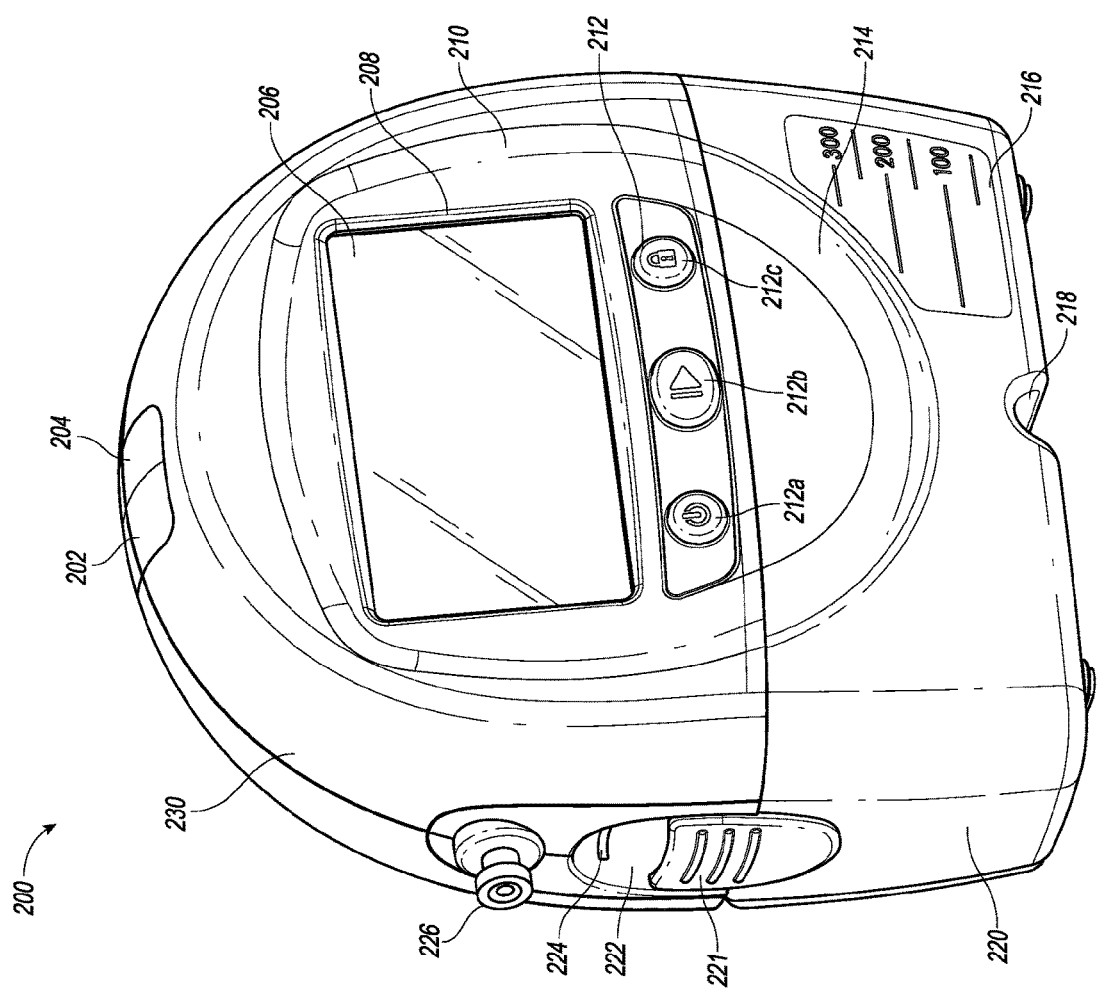
FIG. 2 illustrates a pump assembly and canister according to some embodiments.

FIG. 2 illustrates a front view 200 of a pump assembly 230 and canister 220 according to some embodiments. As is illustrated, the pump assembly 230 and the canister may be connected, thereby forming a TNP device or system. The pump assembly 230 may include one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, no flow condition, canister full condition, or any other similar or suitable conditions or combinations thereof. The pump assembly 230 can include additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 may include a display or screen 206 mounted in a recess 208 formed in a case of the pump assembly. The display 206 can be a touch screen display. The display 206 can support playback of audiovisual (AV) content, such as instructional videos. As explained herein, the display 206 can be configured to render a number of screens or graphical user interfaces (GUIs) for configuring, controlling, and monitoring the operation of the TNP system. The pump assembly 230 includes a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 may include one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 may include one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 includes an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various features are omitted or various additional features are added to the pump assembly 230.

The canister 220 may be configured to hold fluid (e.g., exudate) removed from the wound cavity 110. The canister 220 may include one or more latches 221 for attaching the canister to the pump assembly 230. In the illustrated embodiment, the canister 220 includes two latches 221 on the sides of the canister. The exterior of the canister 220 can formed from frosted plastic so that the canister is substantially opaque and the contents of the canister and substantially hidden from plain view. The canister 220 may include a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 includes a tubing channel 218 for connecting to the conduit 140. In some embodiments, one or more of these features, such as the gripping portion 214, are omitted or various additional features are added to the canister 220. Any of the disclosed canisters may include or may omit a solidifier.

Electronics and Software

Figure 3:
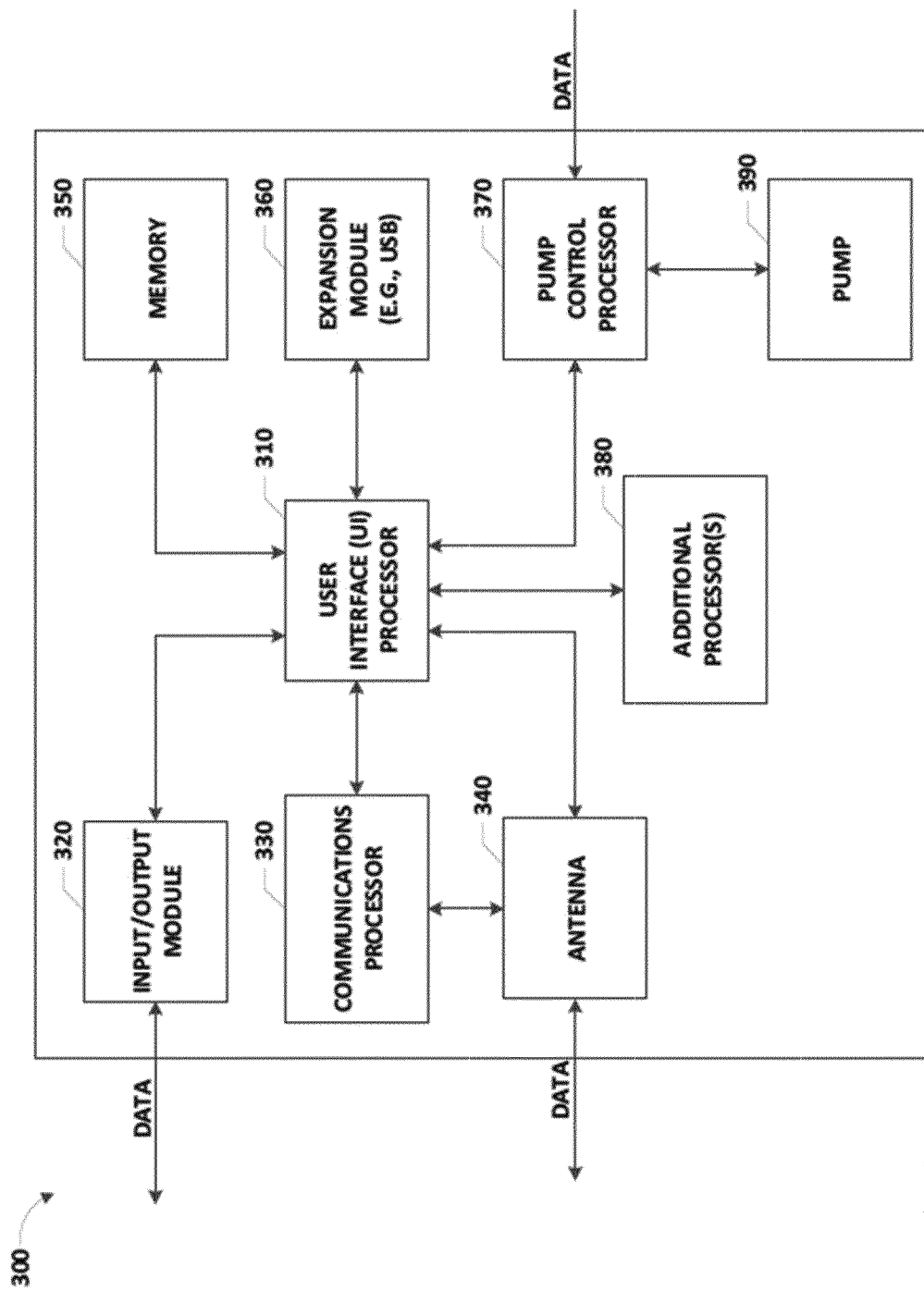
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can include a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, Magnetoresistive random-access memory (MRAM), and the like.

In some embodiments, the processor 310 can be a general-purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure source or pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control an actuator, such as a pump motor, so that a desired level of negative pressure is achieved in the wound cavity 110. The desired level of negative pressure can be pressure set or selected by the user. In various embodiments, the pump control processor 370 controls the pump actuator (e.g., pump motor) using pulse-width modulation (PWM). A control signal for driving the pump actuator can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), Wi-Fi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Flexible Suction Adapter

FIGS. 4A-6 illustrate embodiments of a negative pressure wound treatment system 5501 similar to the embodiment illustrated in FIG. 1. Here, the system 5501 may comprise a flexible suction adapter 5500 having a bridge portion 5502 with a proximal end 5503 and a distal end 5505, and an applicator 5520 at the distal end 5505 of the bridge portion 5502 forming the flexible suction adapter 5500. A connector 5504 is preferably disposed at the proximal end 5503 of the bridge portion 5502, so as to connect to at least one of the channels 5512 and/or 5516, as shown in FIG. 4B. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 may be the pump 200 described in relation to FIG. 2. In some embodiments, this pump 5534 can be a RENASYS GO pump, as sold by Smith & Nephew. The pump 5534 may be connected to the connector 5504 via a tube 5540. In use, the applicator 5520 is placed over an aperture 5535 formed in a drape 5531 that is placed over a suitably-prepared wound 5530, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

In some embodiments, the bridge portion 5502 may comprise an upper channel layer 5512 positioned between an upper layer 5510 and an intermediate layer 5514, with a lower channel layer 5516 positioned between the intermediate layer 5514 and a bottom layer 5518. Preferably, the layers 5510, 5514, and 5518 have elongate portions extending between proximal and distal ends and may be comprised of a material that is fluid-impermeable, for example polymers such as polyurethane. It will of course be appreciated that the layers 5510, 5514, and 5518 may each be constructed from different materials, including semi-permeable materials. In some embodiments, one or more of the layers 5510, 5514, and 5518 may be at least partially transparent. As illustrated in FIG. 5B, the upper and lower layers 5510 and 5518 may be curved, rounded or outwardly convex over a majority of their lengths. During assembly, for example, the layers 5510, 5514, and 5518 may be pinched together to weld or adhere the layers together. In doing so, the proximal ends of the channels 5512 and 5516 may be sandwiched between these layers, thus partially compressing the proximal ends of the channels 5512, 5516 and stretching the layers 5510, 5514, 5518 over these aforementioned proximal ends. Of course, the proximal ends of the materials used in the bridge portion 5502 may not necessarily be rounded or curved; as shown in FIG. 6, they can remain substantially squared off and straight.

The upper and lower channel layers 5512 and 5516 are preferably elongate layers extending from the proximal end 5503 to the distal end 5505 and may each preferably comprise a porous material, including for example open-celled foams such as polyethylene or polyurethane. In some embodiments, one or more of the upper and lower channel layers 5512 and 5516 may be comprised of a fabric, for example a knitted or woven spacer fabric (such as a knitted polyester 3D fabric, Baltex 7970®, or Gehring 879®) or a nonwoven material (e.g., Glatfelter Vizorb® 3055 MBAL90, Daltex® REPEL, and/or a sterilisable thermally bonded nonwoven viscose and polypropylene non-woven fabric such as Freudenberg M1556N or Vilene). Suitable materials may also include terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure and/or vented air to the wound site, and may also confer a degree of kinking or occlusion resistance to the channel layers 5512 and 5516 as described below. In one embodiment, the upper channel layer 5512 may comprise an open-celled foam such as polyurethane, and the lower channel layer may comprise a fabric as described herein. In another embodiment, the upper channel layer is optional, and the system may instead be provided with an open upper channel. In the embodiment illustrated in FIG. 5B, the upper channel layer 5512 may have a curved, rounded or upwardly convex upper surface and a substantially flat lower surface, and the lower channel layer 5516 may have a curved, rounded or downwardly convex lower surface and a substantially flat upper surface.

In some embodiments, the fabric may have a three-dimensional (3D) structure, where one or more types of fibers form a structure where the fibers extend in all three dimensions. Such a fabric may in some cases aid in wicking, transporting fluid, and/or transmitting negative pressure. To prevent the channels 5512 and/or 5516 from being displaced or twisted while encased in the system 5501—which may impair performance of the respective channels under negative pressure—it may in some embodiments be preferable to adhere or otherwise secure the channels 5512 and/or 5516 to one or more of the layers 5510, 5514, and 5518. In certain embodiments, these materials remain open and capable of communicating negative pressure to a wound area under the typical pressures used in negative pressure therapy, for example between 40 to 150 mmHg, although higher and lower values are possible. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Additionally, and as described previously, the materials used in the system 5501 are preferably conformable and soft, which may help to avoid pressure ulcers and other complications which may result from a wound treatment system being pressed against the skin of a patient. Further examples of 3D fabrics are discussed below in FIGS. 7A-C.

Preferably, the distal ends of the layers 5510, 5514, and 5518 and the channel layers 5512 and 5516 are enlarged at their distal ends (to be placed over a wound site), and may form a "teardrop" or other enlarged shape. The distal ends of at least the layers 5512, 5514, 5516, and 5518 may also be provided with at least one through aperture. This aperture may be useful not only for the drainage of wound exudate and for applying negative pressure to the wound, but also during manufacturing of the device, as these apertures may be used to align these respective layers appropriately.

Figure 5A:
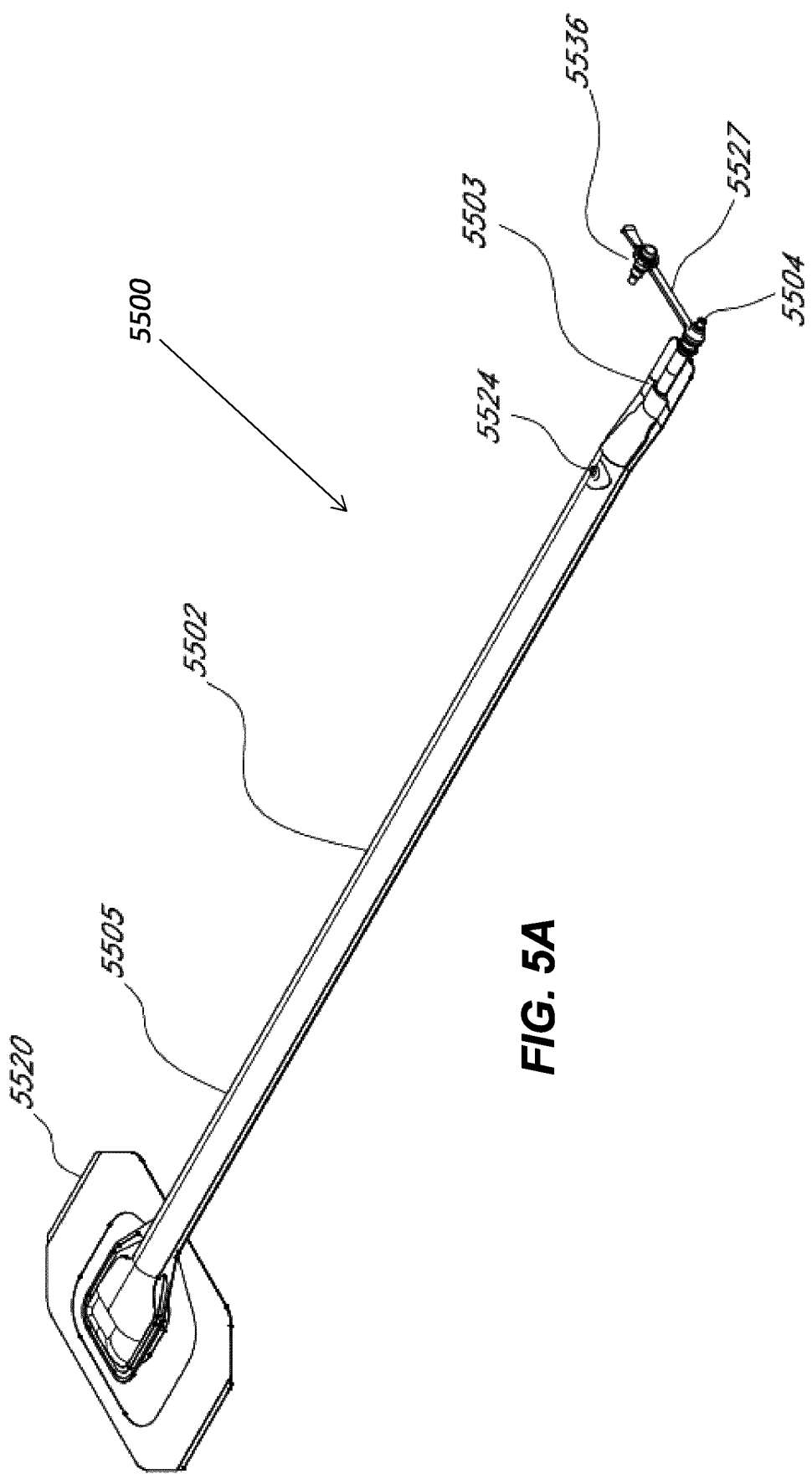
FIG. 5A illustrates an isometric view of a flexible suction adapter that may be used in a negative pressure wound treatment system.
Figure 5B:
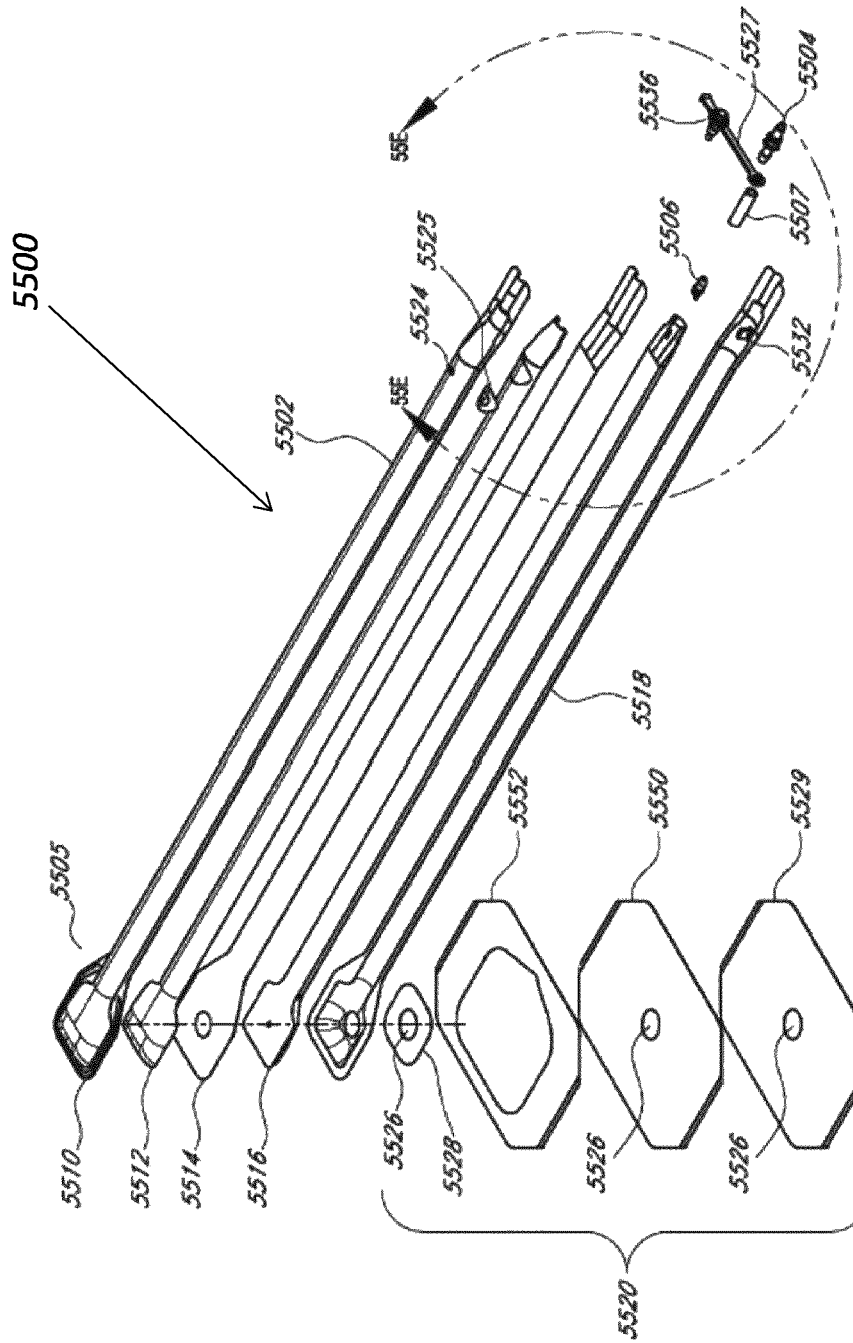
FIG. 5B illustrates an exploded view of the flexible suction adapter of FIG. 5A.
Figure 5C:
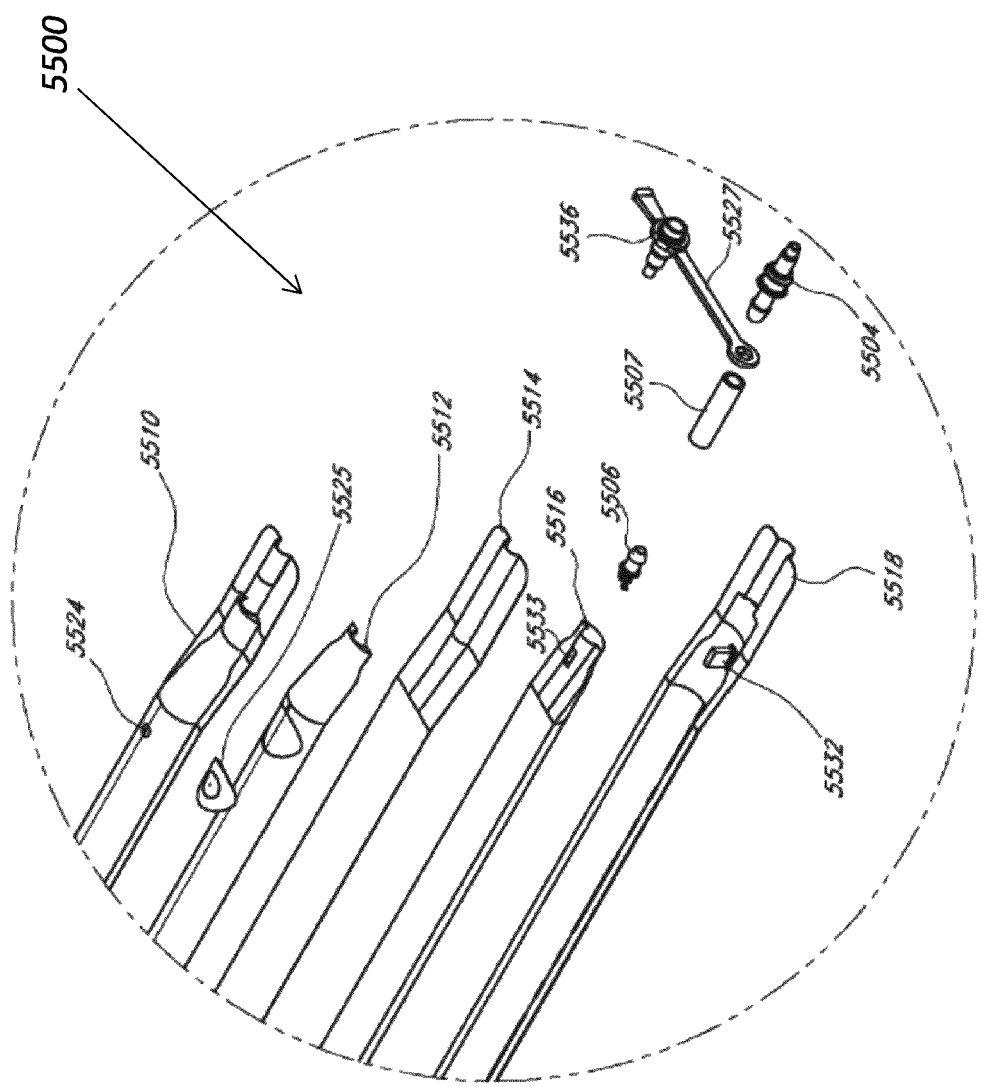
FIG. 5C illustrates a close-up view of the proximal end of the flexible suction adapter of FIG. 5B.
Figure 5D:
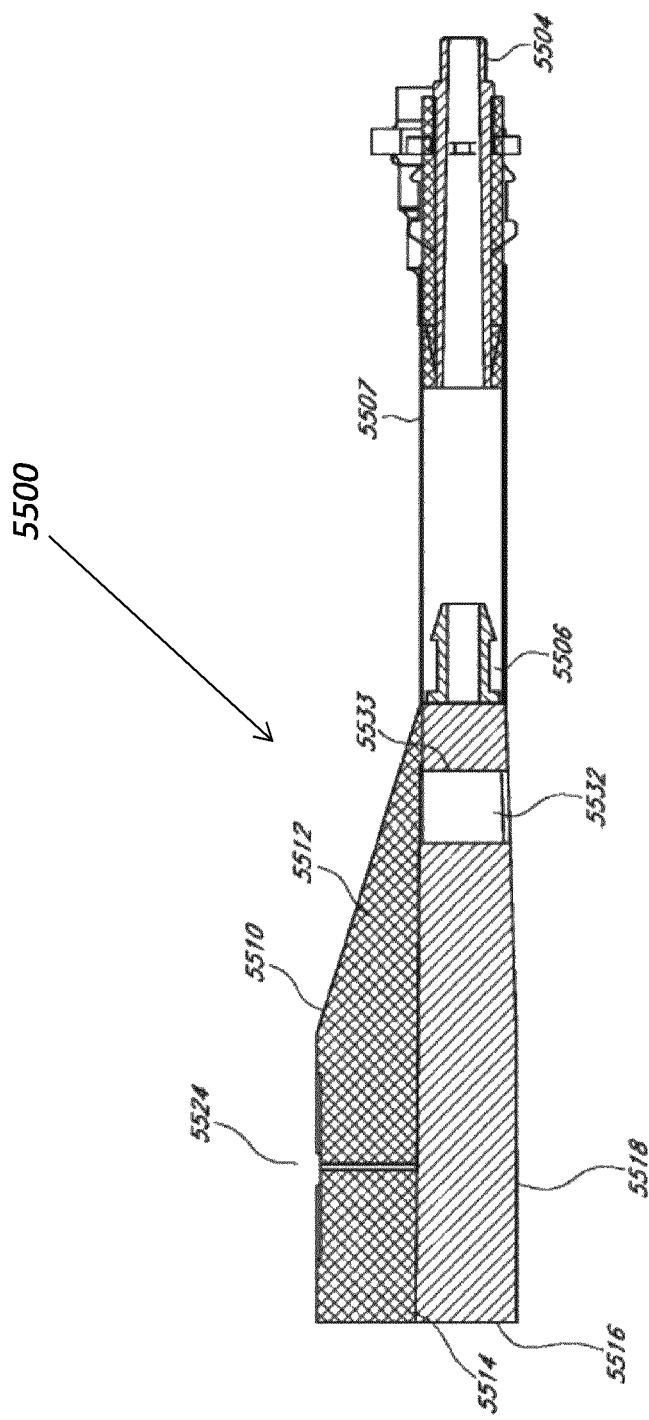
FIG. 5D illustrates a close-up cutaway view of the proximal end of the flexible suction adapter of FIG. 2A.
Figure 5E:
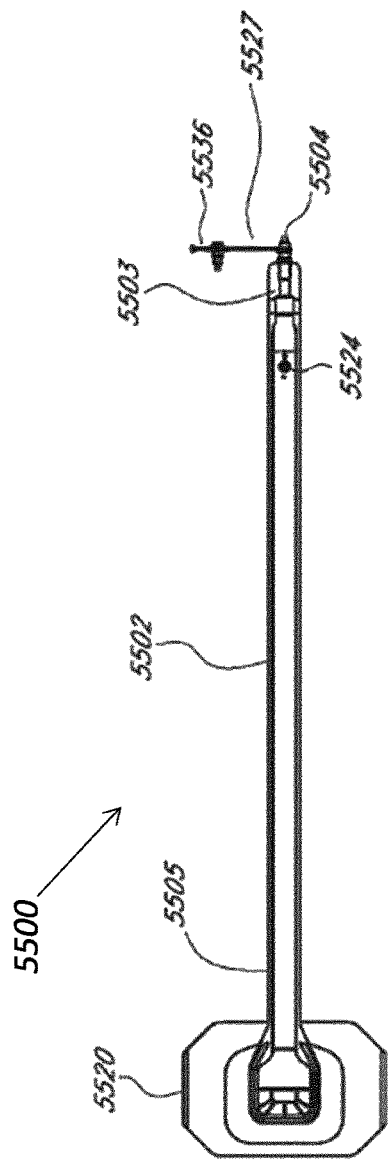
FIG. 5E illustrates a top view of the flexible suction adapter of FIG. 5A.
Figure 5F:
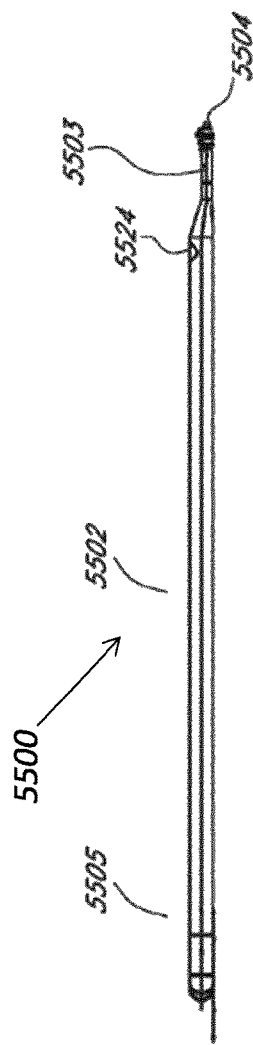
FIG. 5F illustrates a side view of the flexible suction adapter of FIG. 5A.
Figure 5G:
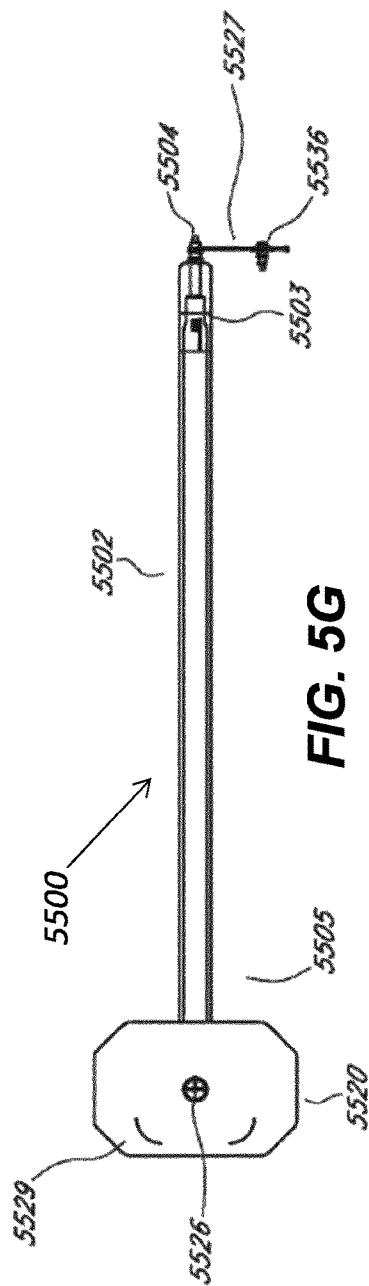
FIG. 5G illustrates a bottom view of the flexible suction adapter of FIG. 5A.
Figure 6:
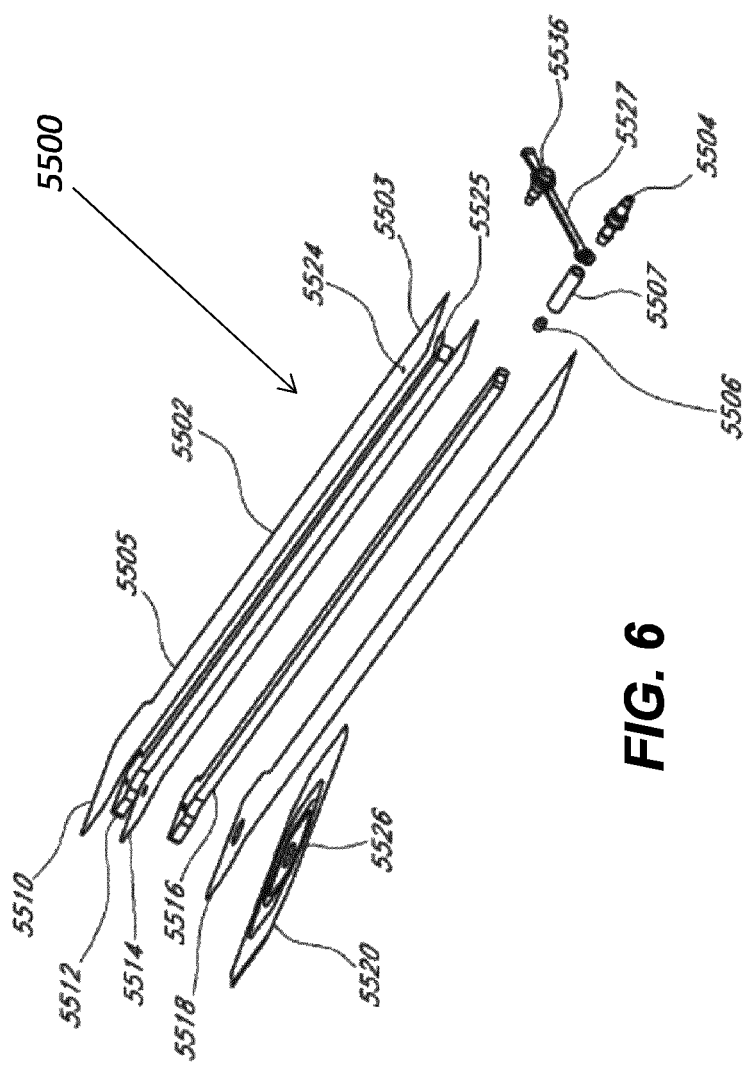
FIG. 6 illustrates an exploded view of an alternative flexible suction adapter.

With additional reference to FIGS. 5B-C and 6, a channel connector 5506 is provided at the proximal end 5503 of the bridge portion 5502, the channel connector 5506 preferably being configured so as to be embedded into the lower channel layer 5516 so as to create a secure fluidic connection. The channel connector 5506 may in some embodiments be inserted into a pre-made cavity formed into the channel 5516; as illustrated in FIG. 6, this cavity can be cut out or can be in the form of a rabbet joint. In some embodiments, the channel connector 5506 may be one of the connectors described in FIGS. 8A-B below. With one end of the channel connector 5506 being embedded into the lower channel layer 5516, the other end of the channel connector 5506 may be connected or in communication with, in one embodiment, a connector tube 5507, although in some embodiments the channel connector 5506 may be connected directly to the connector 5504, or else connected directly to a tube 5540 connected to a source of negative pressure. When using a connector tube 5507, the resulting assembly can permit a connector 5504 to be attached thereto. A cap 5536, which may be secured to the suction adapter for example via a cap leash 5527 secured with a ring disposed on the outer surface of the connector tube 5507. The cap 5536 may be used to cover the end of the suction adapter, for example at the connector 5504, so as to prevent exudate and other wound fluids from leaking out. The connector 5504 is preferably configured to connect with a tube 5540 connected to a source of negative pressure. The connector 5504 may for example comprise a lip or other such structure to aid in securing the connector 5504 to a tube 5540 and/or cap 5536, although it will be understood that other connector types are possible, including quick-disconnect couplings, luer locks, Christmas-tree, and other such connectors.

The upper layer 5510 may comprise additional material extending downward, preferably at least of the thickness of the bridge portion 5502; this material may then be used to bond or weld to the other layers so to form a fluid-tight seal. More specifically, during assembly, the upper layer 5510 may be attached, for example by melting, welding, or with adhesives, to the lower layer 5518 so as to form a fluid-tight seal (with the exception of the apertures at the distal and proximal ends). Preferably, the middle layer 5514 is attached to the top layer 5510 and the bottom layer 5518. In some embodiments, it may be preferable to attach or bond the connectors 5504 and/or 5506, as well as the tube 5507 to at least one of the layers 5510, 5514, 5518 so as to create a fluid-tight connection. To provide for a more secure connection, some embodiments may also be provided with a weld 5532 made onto the lower layer 5518. The lower channel 5516 may have a hole or aperture made through it, which may be used to weld it, via the weld 5532, to the lower layer 5518. This welding of the lower channel 5516 to the lower layer 5518 via the weld 5532 made through the hole 5533 may thus aid in preventing the various layers and channels from shifting or being displaced. Obviously, it will be understood that other securement means may be used, for example adhesives and the like, and that such arrangements may be also be used in the upper channel 5512.

In certain embodiments, for example as illustrated in FIGS. 5A-6, a controlled air leak 5524 may be disposed on the bridge portion 5502, for example at the proximal end thereof. This air leak 5524 may comprise an opening or channel extending through upper layer 5510, such that the air leak 5524 is in fluidic communication with the upper channel 5512. Upon the application of suction to the suction adapter 5500, air will enter through the air leak 5524 and move from the proximal end 5503 to the distal end 5505 along the upper channel 5512. The air will then be suctioned into the lower channel 5516 by passing through the apertures through the distal ends of the layers 5512, 5514, 5516 and 5518. The air leak 5524 preferably comprises a filter 5525. Preferably, the air leak 5524 is located at the proximal end of the bridge portion 5502 so as to minimize the likelihood of wound exudate or other fluids coming into contact and possibly occluding or interfering with the air leak 5524 or its filter 5525. In some embodiments, this filter 5525 is a microporous membrane capable of excluding microorganisms and bacteria, and which may be able to filter out particles larger than 45 µm. Preferably, the filter 5525 can exclude particles larger than 1.0 µm, and more preferably, particles larger than 0.2 µm. Advantageously, some embodiments may provide for a filter 5525 that is at least partially chemically-resistant, for example to water, common household liquids such as shampoos, and other surfactants. In some embodiments, reapplication of vacuum to the suction adapter 5500 and/or wiping of the exposed outer portion of the filter 5525 may be sufficient to clear any foreign substance occluding the filter 5525. The filter 5525 may be composed of a suitably-resistant polymer such as acrylic, polyethersulfone, or polytetrafluoroethylene, and may be oleophobic and/or hydrophobic. In some embodiments, the filter 5525 may also comprise a supporting backing layer, for example a nonwoven polyester support. Preferably, the air leak 5524 will supply a relatively constant air flow that does not appreciably increase as additional negative pressure is applied to the system 5501. In embodiments of the suction adapter 5500 where the air flow through the air leak 5524 increases as additional negative pressure is applied, preferably this increased air flow will be minimized and not increase in proportion to the negative pressure applied thereto.

The filter 5525 provided in the controlled air leak 5524 in certain embodiments may be useful in a system 5501 for use with more ambulatory and active patients. For example, a chemically-resistant filter may permit a patient to bathe or shower without damaging the filter's functionality when reconnected to a source of negative pressure. Any occlusion or fluid blocking the air leak 5524 could then be cleared by, for example, wiping off the filter 5525 or re-applying negative pressure to the suction adapter 5500. Such a system would also have the advantage that the system 5501 and any assorted wound dressing materials, if present, would not need to be removed and then re-applied should a patient need to be disconnected from the source of negative pressure, for example incidental to bathing. This would entail significant advantages in improving the cost-effectiveness and ease of use of the present treatment system.

The suction adapter 5500 is preferably constructed so as to provide a consistent fluid flow even if the suction adapter 5500 is kinked or weighted down. For example, in use on a patient, the bridge portion 5502 may become folded over itself, or else the patient may roll over, thus placing his or her weight over at least a portion of the suction adapter 5500. Typically, prior art dressings and fluidic connectors become blocked or ineffective in such situations and in some cases may contribute to complications such as pressure ulcers. Here, however, certain embodiments provide for improved blockage resistance if kinked or weighed down. Preferably, by employing channel layers 5512 and 5516 as described above, and more preferably by employing a foam channel layer 5512 and a fabric channel layer 5516, the suction adapter 5500 is able to maintain a flow rate through the air leak 5524 of at least 0.08 L/min, and preferably 0.12 L/min while negative pressure is applied through a source of negative pressure. Further embodiments also provide for the suction adapter 5500 to be able to handle fluid exudate drainage from the wound site through the lower channel 5516 of at least 10 L/day, or 6.9 ml/min. Certain embodiments provide for the suction adapter 5500 to maintain these flow rates with a weight, for example a 12 kg weight, pressing down on the bridge portion through a rod with a 1 in. diameter. In some embodiments, these flow rates are also maintained while the bridge portion 5502 is kinked over itself with the same weight, or for example with a 4.75 kg weight placed directly on the folded region. It is preferable that the suction adapter 5500 be able to withstand being folded or kinked over even during an extended period of time, for example over 40 hours, and not show any degradation in performance (e.g., flow rates) compared to its performance prior to being folded or kinked over. Preferably, embodiments of the suction adapter 5500 are also able to transmit and maintain a negative pressure at the wound that is close to the negative pressure level at the source of negative pressure. For example, an acceptable level of pressure maintained at the wound may be within +−0.25 mmHg of the negative pressure set at the source of negative pressure, with this pressure being preferably maintained at this level within 95% of the time that the suction adapter 5500 has negative pressure applied to it. Acceptable pressure levels may include pressure ranges between 40-120 or 125 mmHg, although levels of 200 mmHg have successfully been used.

With additional reference to FIGS. 4A-5B and 6, the suction adapter 5500 also comprises an applicator 5520 designed for placement over a wound site. Preferably, the applicator 5520 comprises a flexible layer 5550, for example polyethylene or polyurethane, with a layer of adhesive on its lower (wound-facing) side. Optionally, a protective release layer 5529 may be placed on the adhesive layer, which is removable before use. In some embodiments, a more rigid removable backing layer 5552 may be provided on the upper side of the applicator 5520 to facilitate handling of the applicator 5520 due to the flexibility of the layer 5550. The applicator 5520 preferably comprises an attachment point for the bridge 5502 at the distal end 5505, for example using a section of double-sided adhesive tape 5528. The double-sided adhesive tape 5528 may be protected by an additional protective release layer, which is removed prior to adhering the bridge 5502 to the applicator 5520. It will be understood that different attachment methods are also contemplated, for example heat sealing, welding, or suitable adhesives. Some embodiments may also permit the manufacture of the bridge 5502 and the applicator 5520 as a single unit that does not require separate attachment means. The applicator 5520 preferably comprises at least one aperture 5526 through itself and designed to be placed over a wound site, and which can serve to fluidically connect the wound site to the source of negative pressure and to the air leak while also serving as a conduit to draw out wound exudate from the wound site.

Figure 4A:
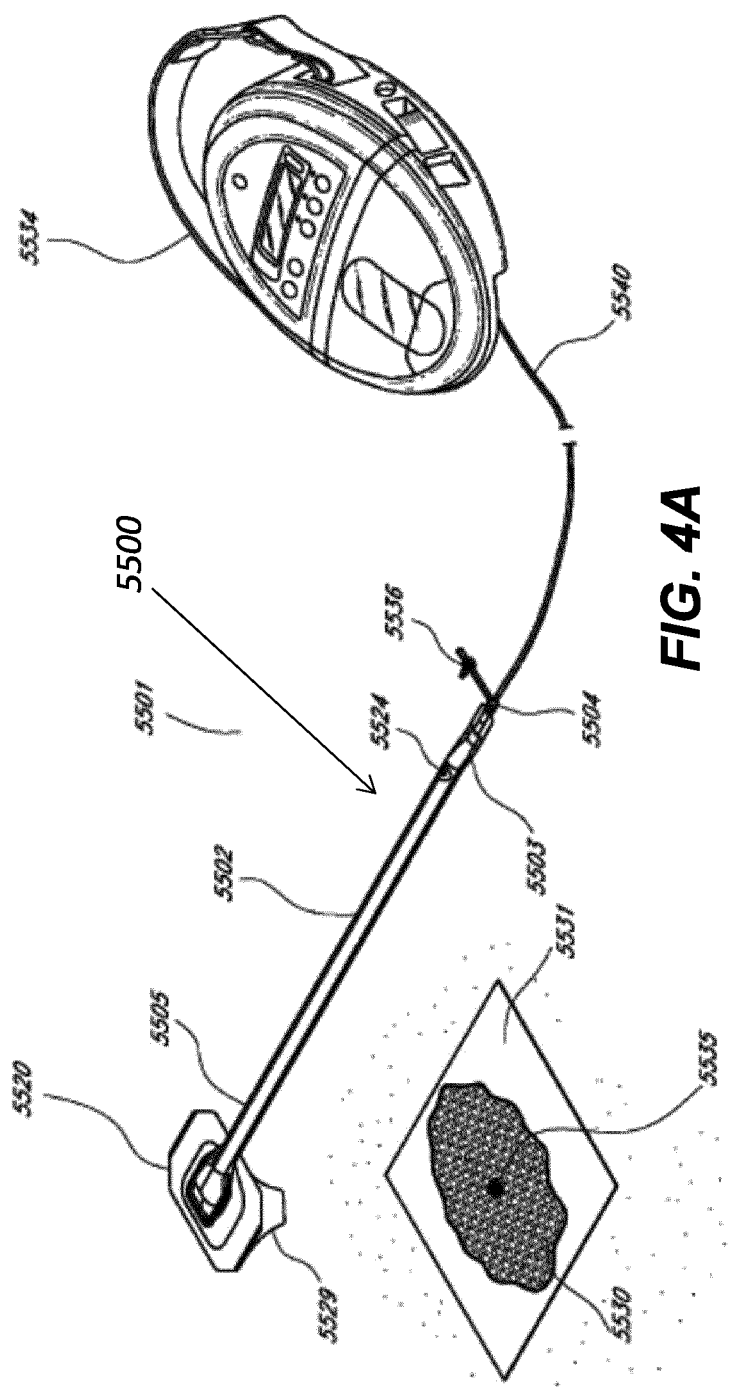
FIG. 4A illustrates an embodiment of a negative pressure wound treatment system comprising a pump, and illustrating a flexible suction adapter being applied to a wound.
Figure 4B:
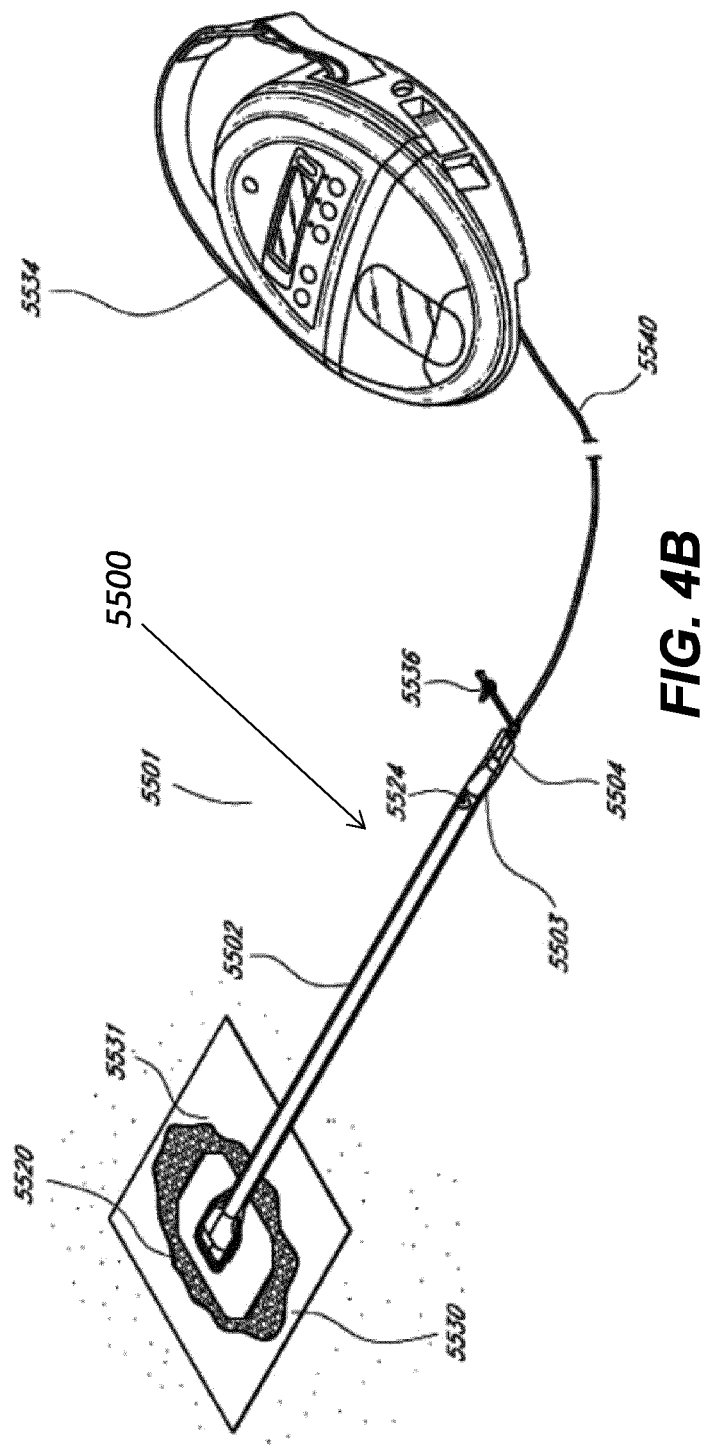
FIG. 4B illustrates the embodiment of FIG. 4A, with the flexible suction adapter having been placed over a wound.

In use, and with reference to FIGS. 4A-B, the system 5501 may be used in a similar fashion to the other embodiments previously disclosed herein, such as the system 100 described in relation to FIG. 1. A wound site 5530 is preferably cleaned and prepared in a suitable fashion, and a wound packing material, if necessary, placed into the wound site, followed by a drape 5531. An aperture 5535 through the drape to the wound site is then created, although some embodiments may have a pre-made aperture 5535. Subsequently, an operator may situate the applicator portion 5520 over the aperture 5535. After removing the backing layer 5529 (if present) from the adhesive layer on the underside of the applicator portion 5520, the applicator is sealed to the drape 5531, and the backing layer 5552 (if present) is also removed from the applicator portion 5520. A fluidic conduit such as a tube 5540 may then be connected to the connector 5504. The tube 5540 may also be connected to connector 5504 prior to applying the applicator to the wound site. The fluidic conduit is connected to a source of negative pressure 5534, preferably with a container suitable for containing wound exudate interposed therebetween. The application of negative pressure may then be effectuated to the wound site 5530 until the wound site progresses to a desired level of healing.

During use of the system 5501, wound exudate from the wound site 5530 is drawn by the negative pressure through the lower channel layer 5516. The air leak 5524 allows air to pass through the upper channel layer 5512 into the apertures through the distal ends of the layers 5512, 5514, 5516 and 5518. The negative pressure draws air passing through the upper channel layer into the lower channel layer 5516 back toward the source of negative pressure or pump. In some embodiments, the controlled air leak 5524 provides a constant flow of air through the suction adapter 5500, which then may be used to determine whether blockage or leakage is present. Causes of blockage can include, for example, situations where the lower channel 5516 becomes occluded with wound debris. Leakage causes can include, for example, improper sealing of the drape over the wound site, or physical damage to the suction adapter 5500 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Multi-Layered Wound Dressings for NPWT

Figure 7A:
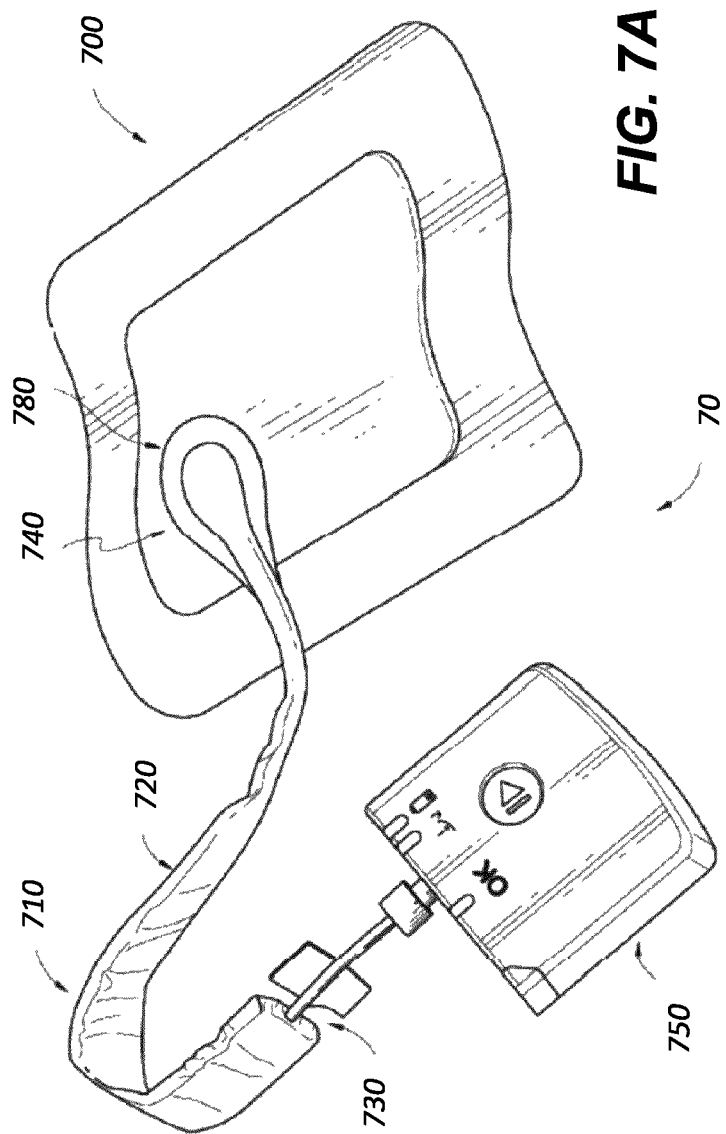
FIG. 7A illustrates an embodiment of a negative pressure wound treatment system employing a pump, a flexible fluidic connector and a wound dressing capable of absorbing and storing wound exudate.

FIG. 7A illustrates an embodiment of a negative pressure wound treatment system 70 employing a wound dressing 700 in conjunction with a fluidic connector 710. Additional examples related to negative pressure wound treatment comprising a wound dressing in combination with a pump as described herein may also be used in combination or in addition to those described in U.S. Pat. No. 9,061,095, which is incorporated by reference in its entirety. Here, the fluidic connector 710 may comprise an elongate conduit, more preferably a bridge 720 having a proximal end 730 and a distal end 740, and an applicator 780 at the distal end 740 of the bridge 720. The system 70 may include a source of negative pressure such as a pump or negative pressure unit 750 capable of supplying negative pressure. The pump may comprise a canister or other container for the storage of wound exudates and other fluids that may be removed from the wound. A canister or container may also be provided separate from the pump. In some embodiments, the pump 750 can be a canisterless pump such as the PICO™ pump, as sold by Smith & Nephew. The pump 750 may be connected to the bridge 720 via a tube, or the pump 750 may be connected directly to the bridge 720. In use, the dressing 700 is placed over a suitably-prepared wound, which may in some cases be filled with a wound packing material such as foam or gauze as described above. The applicator 780 of the fluidic connector 710 has a sealing surface that is placed over an aperture in the dressing 700 and is sealed to the top surface of the dressing 700. Either before, during, or after connection of the fluidic connector 710 to the dressing 700, the pump 750 is connected via the tube to the coupling 760, or is connected directly to the bridge 720. The pump is then activated, thereby supplying negative pressure to the wound. Application of negative pressure may be applied until a desired level of healing of the wound is achieved.

Figure 7B:
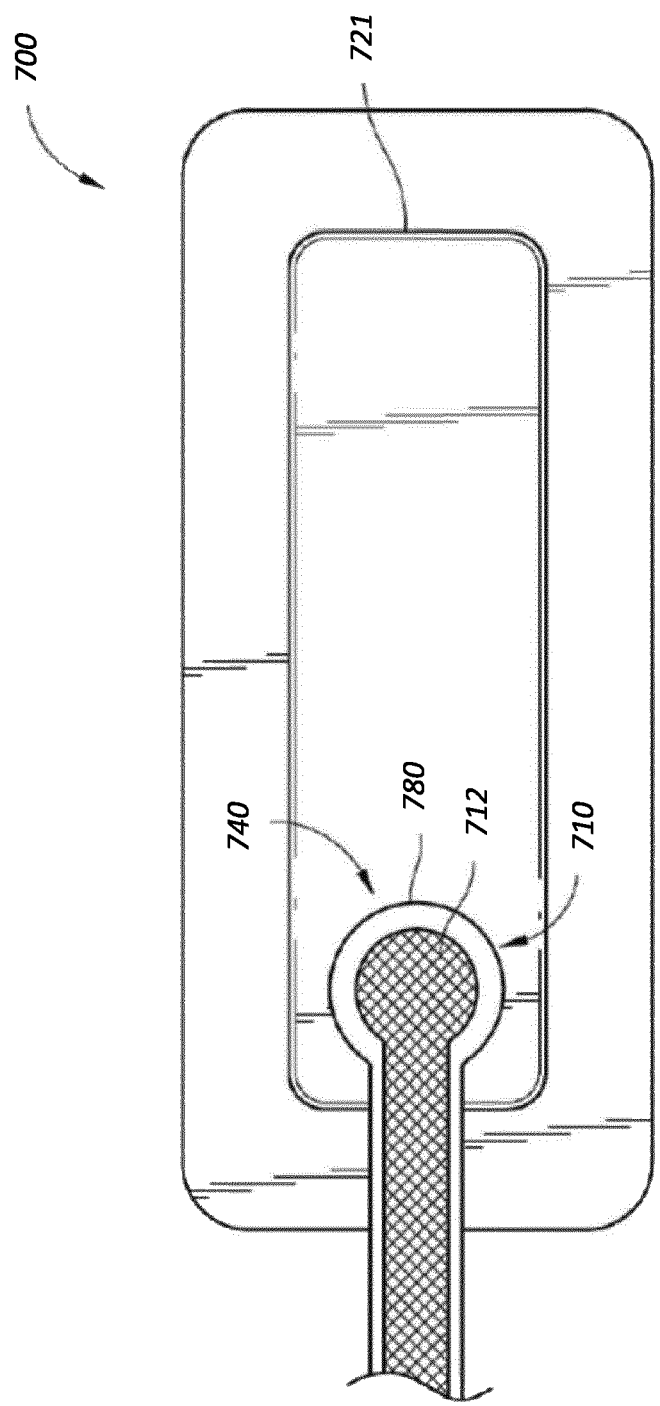
FIG. 7B illustrates an embodiment of a negative pressure wound treatment system employing a flexible fluidic connector and a wound dressing capable of absorbing and storing wound exudate.

As shown in FIG. 7B, the fluidic connector 710 preferably comprises an enlarged distal end, or head 740 that is in fluidic communication with the dressing 700 as will be described in further detail below. In one embodiment, the enlarged distal end has a round or circular shape. The head 740 is illustrated here as being positioned near an edge of the dressing 700, but may also be positioned at any location on the dressing. For example, some embodiments may provide for a centrally or off-centered location not on or near an edge or corner of the dressing 700. In some embodiments, the dressing 70 may comprise two or more fluidic connectors 710, each comprising one or more heads 740, in fluidic communication therewith. In a preferred embodiment, the head 740 may measure 30 mm along its widest edge. The head 740 forms at least in part the applicator 780, described above, that is configured to seal against a top surface of the wound dressing.

Figure 7C:
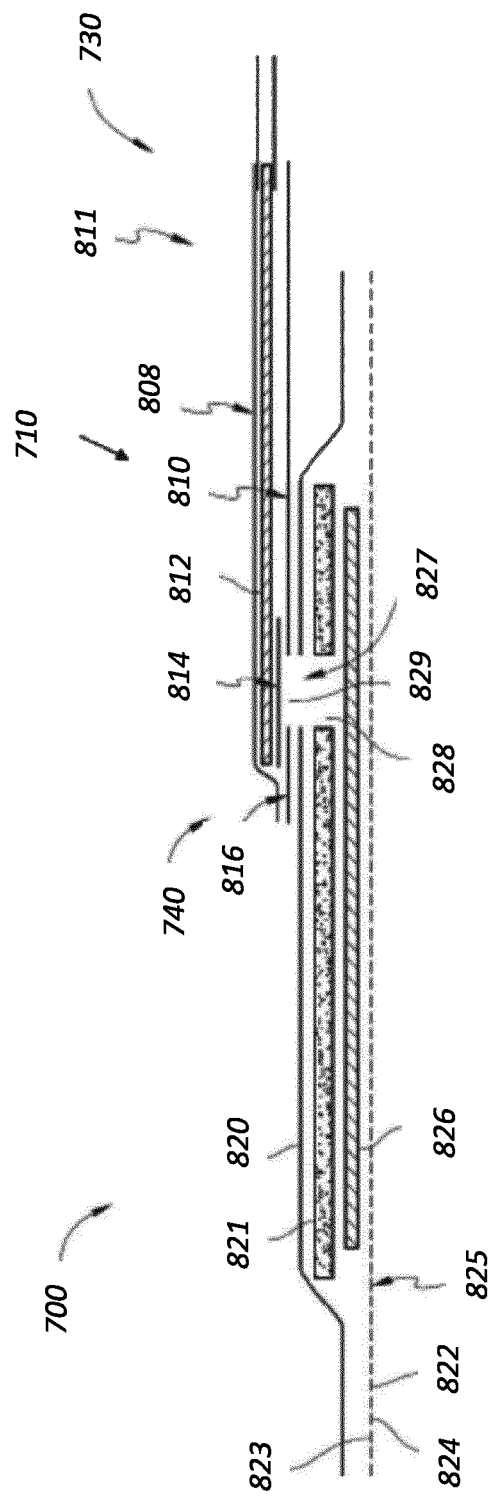
FIG. 7C illustrates a cross section of an embodiment of a fluidic connector connected to a wound dressing.

FIG. 7C illustrates a cross-section through a wound dressing 700 similar to the wound dressing 70 as described in International Patent Publication WO2013175306 A2, which is incorporated by reference in its entirety, along with fluidic connector 710. The wound dressing 700, which can alternatively be any wound dressing embodiment disclosed herein or any combination of features of any number of wound dressing embodiments disclosed herein, can be located over a wound site to be treated. The dressing 700 may be placed as to form a sealed cavity over the wound site. In a preferred embodiment, the dressing 700 comprises a top or cover layer, or backing layer 820 attached to an optional wound contact layer 822, both of which are described in greater detail below. These two layers 820, 822 are preferably joined or sealed together so as to define an interior space or chamber. This interior space or chamber may comprise additional structures that may be adapted to distribute or transmit negative pressure, store wound exudate and other fluids removed from the wound, and other functions which will be explained in greater detail below. Examples of such structures, described below, include a transmission layer 826 and an absorbent layer 821.

As used herein the upper layer, top layer, or layer above refers to a layer furthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

As illustrated in FIG. 7C, the wound contact layer 822 can be a polyurethane layer or polyethylene layer or other flexible layer which is perforated, for example via a hot pin process, laser ablation process, ultrasound process or in some other way or otherwise made permeable to liquid and gas. The wound contact layer 822 has a lower surface 824 and an upper surface 823. The perforations 825 preferably comprise through holes in the wound contact layer 822 which enable fluid to flow through the layer 822. The wound contact layer 822 helps prevent tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 822 may help maintain the integrity of the entire dressing 700 while also creating an air tight seal around the absorbent pad in order to maintain negative pressure at the wound.

Some embodiments of the wound contact layer 822 may also act as a carrier for an optional lower and upper adhesive layer (not shown). For example, a lower pressure sensitive adhesive may be provided on the lower surface 824 of the wound dressing 700 whilst an upper pressure sensitive adhesive layer may be provided on the upper surface 823 of the wound contact layer. The pressure sensitive adhesive, which may be a silicone, hot melt, hydrocolloid or acrylic based adhesive or other such adhesives, may be formed on both sides or optionally on a selected one or none of the sides of the wound contact layer. When a lower pressure sensitive adhesive layer is utilized may be helpful to adhere the wound dressing 700 to the skin around a wound site. In some embodiments, the wound contact layer may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

A transmission layer 826 can be located above the wound contact layer 822. In some embodiments, the transmission layer can be a porous material. As used herein the transmission layer can be referred to as a spacer layer and the terms can be used interchangeably to refer to the same component described herein. This transmission layer 726 allows transmission of fluid including liquid and gas away from a wound site into upper layers of the wound dressing. In particular, the transmission layer 826 preferably ensures that an open-air channel can be maintained to communicate negative pressure over the wound area even when the absorbent layer has absorbed substantial amounts of exudates. The layer 826 should preferably remain open under the typical pressures that will be applied during negative pressure wound therapy as described above, so that the whole wound site sees an equalized negative pressure. The layer 826 may be formed of a material having a three-dimensional structure. For example, a knitted or woven spacer fabric (for example Baltex 7970 weft knitted polyester) or a non-woven fabric could be used. The three-dimensional material can comprise a 3D spacer fabric material similar to the material described in International Publication WO 2013/175306 A2 and International Publication WO2014/020440, the disclosures of which are incorporated by reference in their entireties.

In certain embodiments, the wound dressing 700 may incorporate or comprise a multi-care WCL as described herein this section or elsewhere in the specification. One of skill in the art will understand that the wound dressing 700 may incorporate any of the multi-care WCLs disclosed herein this section or elsewhere in the specification. One of skill in the art will also understand that the multi-care WCL may be incorporated as a whole component layer or a part of a component layer. In some embodiments, the multi-care WCL layer may be provided below the transmission layer 826. In some embodiments, the multi-care WCL layer may be provided above the wound contact layer 822. In some embodiments, the multi-care WCL layer may replace the transmission layer 826, such that the multi-care WCL layer is provided between an absorbent layer 221 (described further below) and the wound contact layer 822. In some embodiments, the multi-care WCL layer can supplement or replace the absorbent layer 821. In some embodiments, the wound dressing 700 does not have the wound contact layer 822, and the multi-care WCL layer may be the lowermost layer of the wound dressing 700. The multi-care WCL may have same or substantially similar size and shape with the transmission layer 826 and/or the absorbent layer 821.

The multi-care WCL layer may be constructed to be flexible but stiff enough to withstand negative pressure, such that the multi-care WCL is not collapsed excessively and thereby transmits negative pressure sufficiently to the wound when negative pressure is supplied to the wound dressing 700. The multi-care WCL layer may be constructed to include sufficient number or size of pores to enable transmission of negative pressure through it. Further, the multi-care WCL layer may have suitable thickness to transmit enough negative pressure to the wound. For example, the multi-care WCL layer may have a thickness of 1 mm to 10 mm, or 1 mm to 7 mm, or 1.5 mm to 7 mm, or 1.5 mm to 4 mm, or 2 mm to 3 mm. In some embodiments, the multi-care WCL may have a thickness of approximately 2 mm.

In some embodiments, the layer 821 of absorbent material is provided above the transmission layer 826. The absorbent material, which can comprise a foam or non-woven natural or synthetic material, and which may optionally comprise a super-absorbent material, forms a reservoir for fluid, particularly liquid, removed from the wound site. In some embodiments, the layer 821 may also aid in drawing fluids towards the backing layer 220.

The material of the absorbent layer 821 may also prevent liquid collected in the wound dressing 700 from flowing freely within the dressing, and preferably acts so as to contain any liquid collected within the dressing. The absorbent layer 821 also helps distribute fluid throughout the layer via a wicking action so that fluid is drawn from the wound site and stored throughout the absorbent layer. This helps prevent agglomeration in areas of the absorbent layer. The capacity of the absorbent material must be sufficient to manage the exudates flow rate of a wound when negative pressure is applied. Since in use the absorbent layer experiences negative pressures the material of the absorbent layer is chosen to absorb liquid under such circumstances. A number of materials exist that are able to absorb liquid when under negative pressure, for example superabsorber material. The absorbent layer 821 may typically be manufactured from ALLEVYN™ foam, Freudenberg 114-224-4 or Chem-Posite™ 11C-450. In some embodiments, the absorbent layer 821 may comprise a composite comprising superabsorbent powder, fibrous material such as cellulose, and bonding fibers. In a preferred embodiment, the composite is an air-laid, thermally-bonded composite.

In some embodiments, the absorbent layer 821 is a layer of non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers leads to strong capillary action in the fibrous pad which helps distribute liquid. In this way, the super-absorbent material is efficiently supplied with liquid. The wicking action also assists in bringing liquid into contact with the upper cover layer to aid increase transpiration rates of the dressing.

An aperture, hole, or orifice 827 is preferably provided in the backing layer 820 to allow a negative pressure to be applied to the dressing 700. The fluidic connector 710 is preferably attached or sealed to the top of the backing layer 820 over the orifice 827 made into the dressing 700, and communicates negative pressure through the orifice 827. A length of tubing may be coupled at a first end to the fluidic connector 710 and at a second end to a pump unit (not shown) to allow fluids to be pumped out of the dressing. Where the fluidic connector is adhered to the top layer of the wound dressing, a length of tubing may be coupled at a first end of the fluidic connector such that the tubing, or conduit, extends away from the fluidic connector parallel or substantially to the top surface of the dressing. The fluidic connector 710 may be adhered and sealed to the backing layer 820 using an adhesive such as an acrylic, cyanoacrylate, epoxy, UV curable or hot melt adhesive. The fluidic connector 710 may be formed from a soft polymer, for example a polyethylene, a polyvinyl chloride, a silicone or polyurethane having a hardness of 30 to 90 on the Shore A scale. In some embodiments, the fluidic connector 710 may be made from a soft or conformable material.

Optionally, the absorbent layer 821 includes at least one through hole 828 located so as to underlie the fluidic connector 710. The through hole 828 may in some embodiments be the same size as the opening 827 in the backing layer, or may be bigger or smaller. As illustrated in FIG. 2C a single through hole can be used to produce an opening underlying the fluidic connector 710. It will be appreciated that multiple openings could alternatively be utilized. Additionally, should more than one port be utilized according to certain embodiments of the present disclosure one or multiple openings may be made in the absorbent layer in registration with each respective fluidic connector. Although not essential to certain embodiments of the present disclosure the use of through holes in the super-absorbent layer may provide a fluid flow pathway which remains unblocked in particular when the absorbent layer is near saturation.

The aperture or through-hole 828 is preferably provided in the absorbent layer 821 beneath the orifice 827 such that the orifice is connected directly to the transmission layer 826 as illustrated in FIG. 2C. This allows the negative pressure applied to the fluidic connector 710 to be communicated to the transmission layer 826 without passing through the absorbent layer 821. This ensures that the negative pressure applied to the wound site is not inhibited by the absorbent layer as it absorbs wound exudates. In other embodiments, no aperture may be provided in the absorbent layer 821, or alternatively a plurality of apertures underlying the orifice 827 may be provided. In further alternative embodiments, additional layers such as another transmission layer or an obscuring layer such as described with reference to FIGS. 6A-6B and in International Patent Publication WO2014/020440, the entirety of which is hereby incorporated by reference, may be provided over the absorbent layer 821 and beneath the backing layer 820.

The backing layer 820 is preferably gas impermeable, but moisture vapor permeable, and can extend across the width of the wound dressing 700. The backing layer 820, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber is made between the backing layer 820 and a wound site where a negative pressure can be established. The backing layer 820 is preferably sealed to the wound contact layer 822 in a border region around the circumference of the dressing, ensuring that no air is drawn in through the border area, for example via adhesive or welding techniques. The backing layer 820 protects the wound from external bacterial contamination (bacterial barrier) and allows liquid from wound exudates to be transferred through the layer and evaporated from the film outer surface. The backing layer 820 preferably comprises two layers; a polyurethane film and an adhesive pattern spread onto the film. The polyurethane film is preferably moisture vapor permeable and may be manufactured from a material that has an increased water transmission rate when wet. In some embodiments, the moisture vapor permeability of the backing layer increases when the backing layer becomes wet. The moisture vapor permeability of the wet backing layer may be up to about ten times more than the moisture vapor permeability of the dry backing layer.

The absorbent layer 821 may be of a greater area than the transmission layer 826, such that the absorbent layer overlaps the edges of the transmission layer 826, thereby ensuring that the transmission layer does not contact the backing layer 820. This provides an outer channel of the absorbent layer 821 that is in direct contact with the wound contact layer 822, which aids more rapid absorption of exudates to the absorbent layer. Furthermore, this outer channel ensures that no liquid is able to pool around the circumference of the wound cavity, which may otherwise seep through the seal around the perimeter of the dressing leading to the formation of leaks. As illustrated in FIG. 7C, the absorbent layer 821 may define a smaller perimeter than that of the backing layer 820, such that a boundary or border region is defined between the edge of the absorbent layer 821 and the edge of the backing layer 820.

As shown in FIG. 7C, one embodiment of the wound dressing 700 comprises an aperture 828 in the absorbent layer 821 situated underneath the fluidic connector 710. In use, for example when negative pressure is applied to the dressing 700, a wound facing portion of the fluidic connector may thus come into contact with the transmission layer 826, which can thus aid in transmitting negative pressure to the wound site even when the absorbent layer 821 is filled with wound fluids. Some embodiments may have the backing layer 820 be at least partly adhered to the transmission layer 826. In some embodiments, the aperture 828 is at least 1-2 mm larger than the diameter of the wound facing portion of the fluidic connector 710, or the orifice 827.

In particular for embodiments with a single fluidic connector 710 and through hole, it may be preferable for the fluidic connector 710 and through hole to be located in an off-center position as illustrated in FIG. 7B. Such a location may permit the dressing 700 to be positioned onto a patient such that the fluidic connector 710 is raised in relation to the remainder of the dressing 700. So positioned, the fluidic connector 710 and the filter 814 may be less likely to come into contact with wound fluids that could prematurely occlude the filter 814 so as to impair the transmission of negative pressure to the wound site.

Similar to the embodiments of wound dressings described above, some wound dressings comprise a perforated wound contact layer with silicone adhesive on the skin-contact face and acrylic adhesive on the reverse. In some embodiments, the wound contact layer may be constructed from polyurethane, polyethylene or polyester. Above this bordered layer sits a transmission layer. Above the transmission layer, sits an absorbent layer. The absorbent layer can include a superabsorbent non-woven (NW) pad. The absorbent layer can over-border the transmission layer by approximately 5 mm at the perimeter. The absorbent layer can have an aperture or through-hole toward one end. The aperture can be about 10 mm in diameter. Over the transmission layer and absorbent layer lies a backing layer. The backing layer can be a high moisture vapor transmission rate (MVTR) film, pattern coated with acrylic adhesive. The high MVTR film and wound contact layer encapsulate the transmission layer and absorbent layer, creating a perimeter border of approximately 20 mm. The backing layer can have a 10 mm aperture that overlies the aperture in the absorbent layer. Above the hole can be bonded a fluidic connector that comprises a liquid-impermeable, gas-permeable semi-permeable membrane (SPM) or filter that overlies the aforementioned apertures.

Wound Dressing for Circumferential Surfaces

Figure 8:
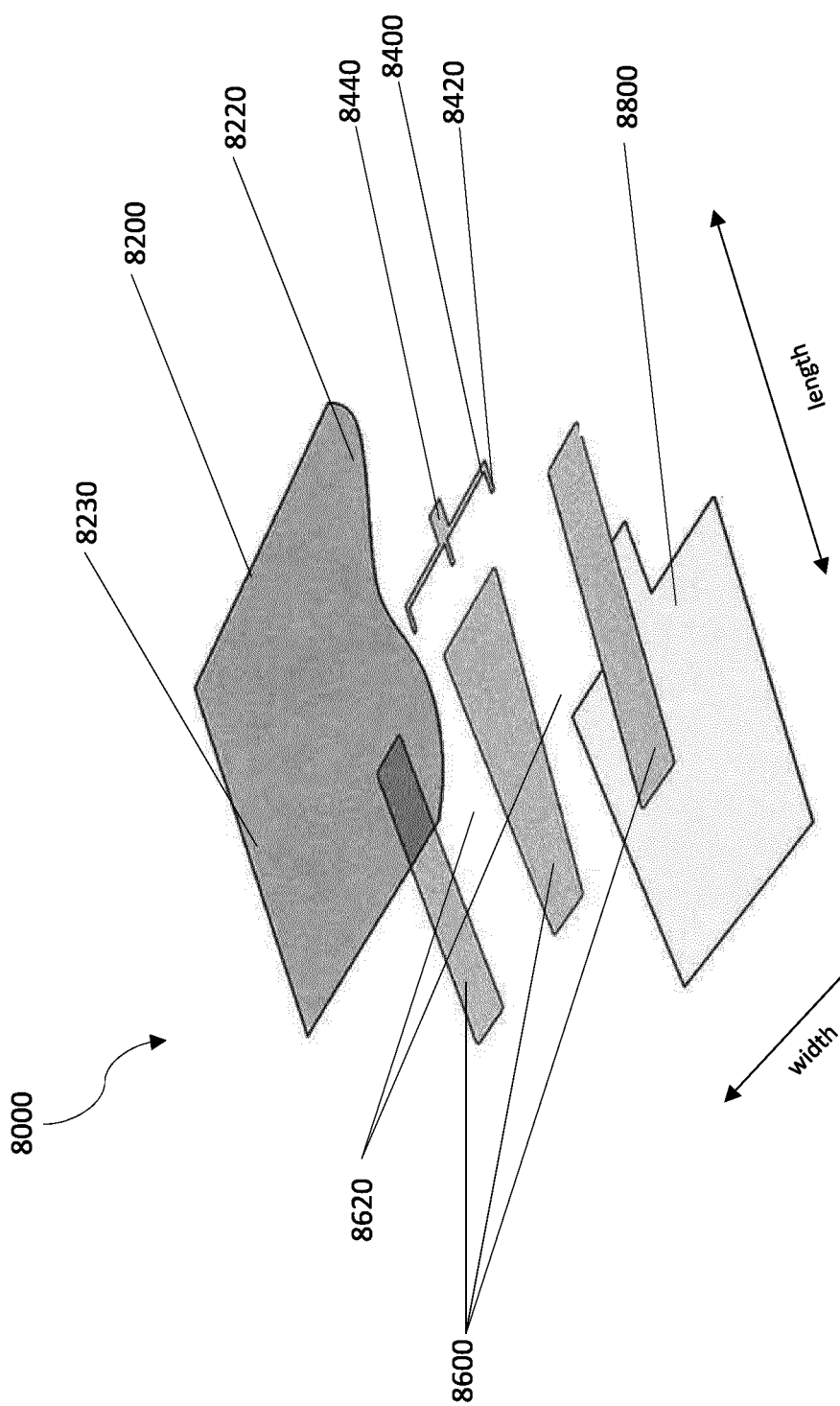
FIG. 8 illustrates an exploded view of an embodiment of a wound dressing according to an embodiment.

FIG. 8 illustrates an example of a wound dressing 8000 for negative pressure wound therapy (NPWT) which can be applied to a circumferential or substantially circumferential surface, such as an arm or a leg. The wound dressing 8000 may be applied to circumferential wounds, such as venous leg ulcers, or severe burns at a limb. In the illustrated embodiment, the wound dressing 8000 includes a cover layer 8200, a plurality of spacer sections 8600, a connector 8400 and a wound contact layer 8800. As illustrated in FIG. 8, the wound dressing 8000 may have a length extending between a proximal end and a distal end, and a width perpendicular to the length. When the wound dressing 8000 is applied to a circumferential surface, the width of the wound dressing 8000 may wrap around the circumferential surface along the circumference, while the length of the wound dressing 8000 may extend parallel or substantially parallel to a length of the circumferential surface perpendicular to the circumference. The application of the wound dressing 8000 is further explained in greater detail herein.

In some embodiments, the wound contact layer 8800 is the lowermost layer of the wound dressing 8000 and may act as the primary interface between a wound and the wound dressing 8000. The wound contact layer 8800 may be similar to any wound contact layers described elsewhere herein, such as the wound contact layer 822. For example, the wound contact layer 8800 may be a polyurethane layer or polyethylene layer or other flexible layer which is perforated, for example via a hot pin process, laser ablation process, ultrasound process or in some other way or otherwise made permeable to liquid and gas. The perforations may comprise through holes in the wound contact layer 8800 which enable fluid to flow through the wound contact layer 8800. The wound contact layer 8800 may help preventing tissue ingrowth into the other material of the wound dressing. Preferably, the perforations are small enough to meet this requirement while still allowing fluid to flow therethrough. For example, perforations formed as slits or holes having a size ranging from 0.025 mm to 1.2 mm are considered small enough to help prevent tissue ingrowth into the wound dressing while allowing wound exudate to flow into the dressing. In some configurations, the wound contact layer 8800 may help maintain the integrity of the wound dressing 8000 while also creating an airtight seal around the wound in order to maintain negative pressure at the wound. In operation, the wound contact layer 8800 may provide unidirectional flow so as to facilitate removal of exudate from the wound while blocking or substantially preventing exudate from returning to the wound.

The wound contact layer 8800 can include an adhesive on the patient facing side for securing the dressing to the surrounding skin or on the top side for securing the wound contact layer to a cover layer or other layer of the dressing. Some embodiments of the wound contact layer 8800 may also act as a carrier for an optional lower and upper adhesive layer (not shown). For example, a lower pressure sensitive adhesive may be provided on the lower surface of the wound dressing 8000 whilst an upper pressure sensitive adhesive layer may be provided on the upper surface of the wound contact layer 8800. The pressure sensitive adhesive, which may be a silicone, hot melt, hydrocolloid or acrylic based adhesive or other such adhesive, may be formed on both sides or optionally on a selected one or none of the sides of the wound contact layer 8800. When a lower pressure sensitive adhesive layer is utilized may be helpful to adhere the wound dressing 8000 to the skin around a wound site. Further, the lower adhesive layer may allow the wound contact layer 8800 to be applied and repositioned with minimal pain to the patient. In some embodiments, the wound contact layer 8800 may comprise perforated polyurethane film. The lower surface of the film may be provided with a silicone pressure sensitive adhesive and the upper surface may be provided with an acrylic pressure sensitive adhesive, which may help the dressing maintain its integrity. In some embodiments, a polyurethane film layer may be provided with an adhesive layer on both its upper surface and lower surface, and all three layers may be perforated together.

In some embodiments, the cover layer 8200 may be a top layer of the wound dressing 8000 and extend across the width of the wound dressing 8000. The cover layer 8200 may be similar to any cover layers, backing layers and drapes described elsewhere herein, such as the backing layer 820. For example, in some embodiments, the cover layer 8200, which may for example be a polyurethane film (for example, Elastollan SP9109) having a pressure sensitive adhesive on one side, is impermeable to gas and this layer thus operates to cover the wound and to seal a wound cavity over which the wound dressing is placed. In this way, an effective chamber can be made between the cover layer 8200 and a wound site where a negative pressure can be established. In some embodiments, the cover layer can include a moisture vapor permeable material that prevents liquid exudate removed from the wound and other liquids from passing through, while allowing gases through.

The cover layer 8200 may be sealed to the wound contact layer 8800 in a border region around the circumference of the cover layer 8200, ensuring that no air is drawn in through the border area, for example via adhesive or welding techniques. The cover layer 8200 can protect the wound from external bacterial contamination (bacterial barrier) and/or allow liquid from wound exudates to be transferred through the layer and evaporated from the film outer surface. The cover layer 8200 may comprise two layers; a polyurethane film and an adhesive pattern spread onto the film. In some embodiments, the cover layer 8200 may not include an adhesive coating. The polyurethane film may be moisture vapor permeable and may be manufactured from a material that has an increased water transmission rate when wet. In some embodiments, the moisture vapor permeability of the cover layer 8200 increases when the cover layer 8200 becomes wet. The moisture vapor permeability of the wet cover layer may be up to about ten times more than the moisture vapor permeability of the dry cover layer. In some embodiments, the cover layer 8200 is transparent or translucent.

In some embodiments, the cover layer 8200 may have a perimeter larger than the wound contact layer 8800 and/or other layers of the wound dressing 8000, such that the cover layer 8200 can seal around the tissue around the wound. In some embodiments, a width of the cover layer 8200 may be greater than the wound contact layer 8800 and/or other layer of the wound dressing 8000, and/or greater than the circumference of the circumferential surface where the wound dressing 8000 is applied, such that the cover layer 8000 wraps around the circumferential surface and an end of the cover layer 8200 overlaps with the other end of the cover layer 8200. Such an overlap would ensure that the airtight seal is formed around the circumferential surface by the cover layer 8200. In some embodiments, the cover layer 8200 may include an extension portion 8220 extending along the length of the cover layer 8200 at one end as shown in FIG. 8. When the wound dressing 8000 is applied to the circumferential surface, the extension portion 8220 can overlap with an attachment portion 8230 adjacent the opposite end of the cover layer 8000. In some embodiments, the extension portion 8220 may overlap over the attachment portion 8230 of the cover layer 8200. In some embodiments, the extension portion 8220 may overlap below the attachment portion 8230 of the cover layer 8200. In some embodiments, the extension portion 8220 may be attached to the attachment portion 8230 by the adhesive. For example, the extension portion 8220 may have an adhesive coating at a wound facing surface, such that the extension portion 8220 can be attached over the attachment portion 8230. The application of the wound dressing 8000 is further explained in greater detail herein.

Figure 9:
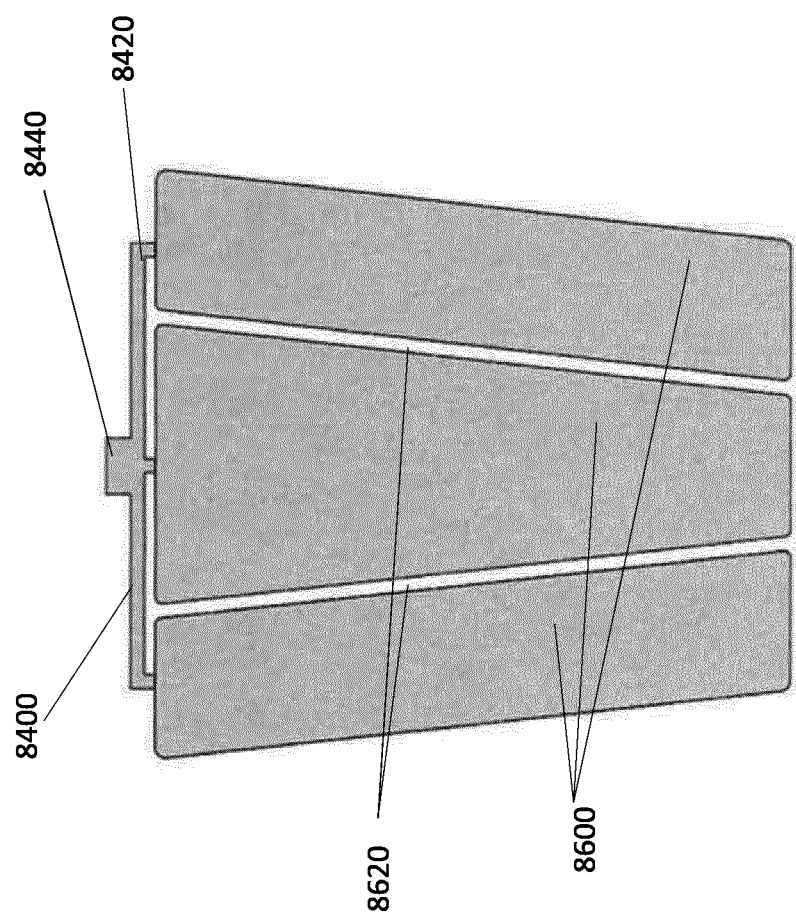
FIG. 9 illustrates a top view of components of the wound dressing of FIG. 8.

As shown in FIG. 8, the plurality of spacer sections 8600 may be positioned between the cover layer 8200 and the wound contact layer 8800. As will be explained further below, the plurality of spacer sections 8600 can assist in distributing negative pressure evenly to the wound surface and/or wicking exudate away from the wound and/or periwound into upper layers of the wound dressing 8000. FIG. 9 illustrates the plurality of spacer sections 8600 and the connector 8400. In some embodiments, each of the plurality of spacer sections 8600 may have an elongate shape having a length extending between a proximal end and a distal end along the length of the wound dressing 8000, and a width extending along the width of the wound dressing 8000. In some embodiments, one or more of the spacer sections 8600 may have a length greater than a width. In some embodiments, one or more of the spacer sections 8600 may have a length same with or similar to a width. In some embodiments, one or more of the spacer sections 8600 may have a length smaller than a width. In some embodiments, each of the spacer sections 8600 may have a same length and/or a same width with other spacer sections 8600. In some embodiments, one or more of the spacer sections 8600 may have a rectangular, substantially rectangular, trapezoidal, or substantially trapezoidal shape. In some embodiments, one or more of the spacer sections 8600 may have a larger or smaller width at the proximal end than the width at the distal end to accommodate different circumferences at different locations of the circumferential surface, such as a limb. In some embodiments, each of the spacer sections 8600 may have a same or substantially same shape with other spacer sections 8600.

Figure 10:
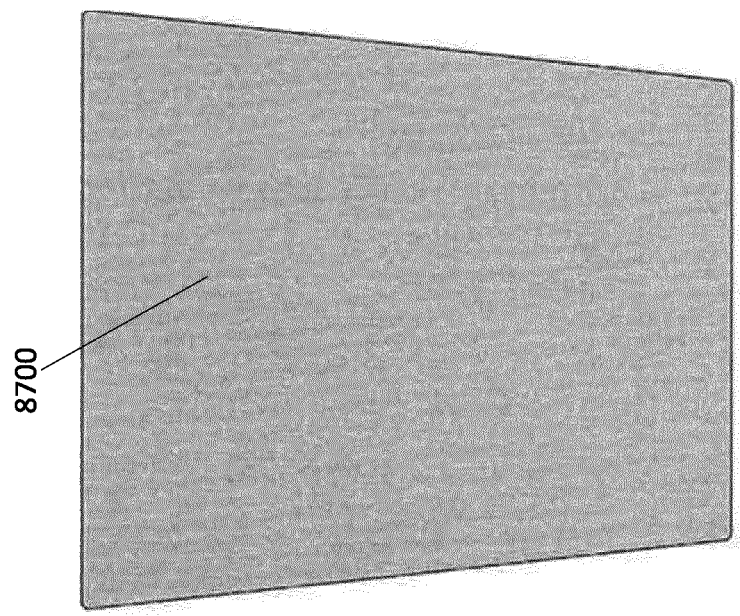
FIG. 10 illustrates a top view of an embodiment of a spacer layer.

In some embodiments, the wound dressing 8000 may include one, two, three, four, five, six, seven, eight, nine, ten or more spacer sections 8600. In the illustrated embodiment, the plurality of spacer sections 8600 are positioned next to one another such that there are multiple spacer sections along the width of the wound dressing 8000, while each spacer sections extends along the length of the wound dressing 8000. In some embodiments, the plurality of spacer sections 8600 may be replaced with a single spacer layer, such as a spacer layer 8700 shown in FIG. 10.

In some embodiments, each of the plurality of spacer sections 8600 may be spaced away from other spacer section positioned adjacently. For example, in the illustrated embodiment, the plurality of spacer sections 8600 are positioned to have gap regions 8620 between each of the plurality of spacer sections 8600, such that each spacer section 8600 are separated by the gap region 8620. In some embodiments, the cover layer 8200 and the wound contact layer 8800 are sealed together at least at a portion of the gap regions 8620. In some embodiments, the cover layer 8200 and the wound contact layer 8800 are sealed together throughout the gap regions 8620 and around each of the plurality spacer sections 8600, such that that each of the plurality of spacer sections 8600 are fluidically isolated from the other spacer sections except for at the connector 8400.

Each of the plurality of spacer sections 8600 may be similar with any spacer layer or transmission layer described elsewhere herein, such as the transmission layer 826. For example, the spacer sections 8600 can be formed of a porous material. Each of the spacer sections 8600 preferably ensures that an open-air channel can be maintained to communicate negative pressure over the wound area. The spacer sections 8600 may remain open under the typical pressures that will be applied during negative pressure wound therapy as described above, such that the whole wound site sees an equalized negative pressure. The spacer sections 8600 may be formed of a material having a three-dimensional structure. For example, a knitted or woven spacer fabric (for example Baltex 7970 weft knitted polyester, a knitted polyester 3D fabric, Baltex 7970®, or Gehring 879®) or a non-woven fabric (e.g., Glatfelter Vizorb® 3055 MBAL90, Daltex® REPEL, and/or a sterilisable thermally bonded nonwoven viscose and polypropylene non-woven fabric such as Freudenberg M1556N or Vilene) could be used. Suitable materials may also include terry-woven or loop-pile materials. The fibers may not necessarily be woven, and can include felted and flocked (including materials such as Flotex®) fibrous materials. The three-dimensional material can comprise a 3D spacer fabric material similar to the material described in International Publication WO 2013/175306 A2 and International Publication WO2014/020440, the disclosures of which are incorporated by reference in their entireties.

Some configurations of the spacer sections 8600 may additionally or alternatively comprise a wicking or acquisition distribution layer (ADL). The ADL is another type of transmission layer that may be provided for communicating fluid through the dressing 8000. The ADL may be configured to horizontally wick fluid such as wound exudate as it is absorbed upward through the layers of the dressing 8000. Lateral wicking of fluid may advantageously increase moisture vapor permeation and efficient delivery of negative pressure to the wound site. Some embodiments of the ADL may comprise viscose, polyester, polypropylene, polyethylene, cellulose (for example polysaccharide or repeated disaccharide), or a combination of some or all of these, and the material may be needle-punched. Some configurations of the ADL may comprise polyethylene in the range of 40-150 grams per square meter (gsm). Some configurations of the ADL may comprise a heavy fibrous melt material. Some configurations of the ADL may be relatively porous to allow for the passage of fluids, including gas, therethrough. One example of an ADL may comprise a lightweight, felt-like, viscose material, which may be 80 gsm (or approximately 80 gsm). Some embodiments of the ADL may comprise cellulose in the range of 40-160 gsm (or about 40 to about 160 gsm), for example 80 (or about 80) gsm. The ADL may be constructed from a material which resists compression under the levels of negative pressure commonly applied during negative pressure therapy. The ADL may be constructed so as to advantageously vertically wick fluid, such as wound exudate. Facilitating rapid movement of wound exudate from the transmission layer to a port on, for example, the cover layer 8200 is desirable. Additionally judicious choice of material can reduce re-wetting of liquid from the upper layers down into lower layers, this phenomenon is known as "back wetting" or "re-wetting". Suitable materials that show an enhancement of this effect include Slimcore TL4 (150 gsm) from Libeltex BVBA or equivalent.

Some configurations of the ADL may include several internal layers. For example, one material suitable for use as an ADL includes a lower wicking or acquisition layer comprising substantially vertically extending fibers for vertical wicking of fluid and further includes an upper distribution layer comprising substantially horizontally extending fibers for horizontal wicking of fluid. Some ADL materials can include three or more layers, for example a lower wicking layer and two upper distribution layers. Other configurations can have one or more distribution layers positioned between upper and lower acquisition layers.

In some embodiments, the spacer sections 8600 may additionally or alternatively comprise an absorbent material, and in other embodiments, the spacer sections 8600 may not have any absorbent material. If absorbent material is utilized, the absorbent material may be a foam or non-woven natural or synthetic material and which may optionally include or be super-absorbent material forms a reservoir for fluid, particularly liquid, removed from the wound site. The material of the spacer sections 8600 also prevents liquid collected in the dressing 8000 from flowing in a sloshing manner. The spacer sections 8600 can help distribute fluid throughout the spacer sections 8600 via a wicking action so that fluid is drawn from the wound site and stored throughout the spacer sections 8600. This can help prevent agglomeration in areas of the spacer sections 8600. The capacity of the absorbent material must be sufficient to manage the exudates flow rate of a wound when negative pressure is applied. Since in use the spacer sections 8600 experiences negative pressures the material of the spacer sections 8600 is chosen to absorb liquid under such circumstances. A number of materials exist that are able to absorb liquid when under negative pressure, for example superabsorber material. In addition to materials described above, the spacer sections 8600 may be manufactured from or comprise ALLEVYN™ foam, Freudenberg 114-224-4 and/or Chem-Posite™ 11C-450.

In some configurations, the spacer sections 8600 can include non-woven cellulose fibers having super-absorbent material in the form of dry particles dispersed throughout. Use of the cellulose fibers introduces fast wicking elements which help quickly and evenly distribute liquid taken up by the dressing. The juxtaposition of multiple strand-like fibers may lead to strong capillary action in the fibrous pad which helps distribute liquid. In this way, the super-absorbent material is efficiently supplied with liquid. Also, all regions of the spacer sections 86000 are provided with liquid. The wicking action also assists in bringing liquid into contact with the cover layer 8200 to aid increase transpiration rates of the dressing 8000. The wicking action may also assist in delivering liquid downwards towards the wound bed when exudation slows or halts. This delivery process can help maintain the spacer sections 8600 and lower wound bed region in a moist state which helps prevent crusting within the dressing 8000, which could lead to blockages, and helps maintain an environment optimized for wound healing.

In some configurations, the spacer sections 8600 may include an air-laid material or any suitable material disclosed herein. Heat fusible fibers may optionally be used to assist in holding the structure of the dressing 8000 together. It will be appreciated that rather than using super-absorbing particles or in addition to such use, super-absorbing fibers may be utilized according to certain configurations of the present disclosure. An example of a suitable material is the Product Chem-Posite™ 11 C available from Emerging Technologies Inc (ETi) in the USA.

Optionally, according to certain configurations of the present disclosure, the spacer sections 8600 may include synthetic stable fibers and/or bi-component stable fibers and/or natural stable fibers and/or super-absorbent fibers. Fibers in the spacer sections 8600 may be secured together by latex bonding or thermal bonding or hydrogen bonding or a combination of any bonding technique or other securing mechanism. In some configurations, the spacer sections 8600 may be formed by fibers which operate to lock super-absorbent particles within the spacer sections 8600. Such an arrangement can help ensure that super-absorbent particles do not move external to the spacer sections 8600 and towards an underlying wound bed. This may improve functionality because when negative pressure is applied there is a tendency for the spacer sections 8600 to collapse downwards and this action may push super-absorbent particle matter into a direction towards the wound bed if they were not locked away by the fibrous structure of the spacer sections 8600.

The spacer sections 8600 may comprise multiple fibers. The fibers can be strand-like and made from cellulose, polyester, viscose or the like. Dry absorbent particles can be distributed throughout the spacer sections 8600 ready for use. In some configurations, the spacer sections 8600 includes a pad of cellulose fibers and a plurality of super absorbent particles. In additional configurations, the spacer sections 8600 can be a non-woven layer of randomly orientated cellulose fibers.

Further details regarding the materials and dressings of this embodiment may be found in International Application PCT/EP2020/078376 ("App. '376") filed on Oct. 9, 2020 and International Application PCT/EP2021/058696 ("App. '696") filed on Apr. 1, 2021, the disclosures of which are incorporated by reference in their entireties including, but not limited to, the description accompanying FIGS. 12A-12B of App. '376, and FIGS. 13A-13B of App. '696. For example, the materials described for the top layers 1310, 1410, 1410' as shown in FIGS. 12A-12B and FIGS. 13A-13B can be interchanged with the cover layer 8200. The materials described for the wound contact layer 1330, 1430 as shown in FIGS. 12A and 13A can be interchanged with the wound contact layer 8800. The materials described for the transmission layer 1340, 1440 as shown in FIGS. 12A and 13A can be interchanged with the spacer sections 8600.

In some embodiments, a further layer may be provided for the dressings disclosed herein. For example, the additional layer may be a protective construction layer (also referred to herein as PCL) provided between the spacer sections 8600 and the cover layer 8200. The PCL can be configured to provide support to the dressing 8000 and protect the cover layer 8200 from the spacer sections 8600. Some configurations of the PCL may comprise polypropylene spunbond material. For example, the PCL can be manufactured from or comprise Glatfelter Vizorb® 3055 MBAL90, Daltex® REPEL, and/or a sterilisable thermally bonded nonwoven viscose and polypropylene non-woven fabric (e.g., Freudenberg M1556N, Vilene). Further, some configurations of the PCL may comprise a hydrophobic additive or coating. Some configurations may comprise a thin fibrous sheet of 60, 70, or 80 gsm. Further details regarding the PCL may be found in International Application PCT/EP2020/078376 ("App. '376") filed on Oct. 9, 2020 and International Application PCT/EP2021/058696 ("App. '696") filed on Apr. 1, 2021, the disclosures of which are incorporated by reference in their entireties including, but not limited to, the description accompanying FIGS. 12A-12B of App. '376, and FIGS. 13A-13B of App. '696.

As shown in FIGS. 8-9, the connector 8400 may be positioned at the proximal end of the spacer sections 8600 and directly and/or fluidically connected to the spacer sections 8600. In some embodiments, the connector 8400 may be positioned at the distal end of the spacer sections 8600. The connector 8400 may include a plurality of inlets 8420, and each of the inlets 8420 can be connected to the proximal end of one of the spacer sections 8600. In the illustrated embodiment, the connector 8400 includes an outlet 8440 adjacent to the proximal end of the dressing 8000, and the outlet 8440 may be fluidically connected to a source of negative pressure. In some embodiments, the outlet 8440 may be connected to a connection mean (e.g. port, tube, vacuum connector) to connect to a conduit which can be connected to the source of negative pressure. For example, the outlet 8440 may be coupled with a tube extending through the proximal end of the dressing 8000, and the cover layer 8200 and the wound contact layer 8800 can be sealed around the outlet 8440 and the tube, such that the tube can be further connected to the source of negative pressure via the conduit. In some embodiments, the cover layer 8200 includes one or more opening above the outlet 8440, such that a port, a fluidic connector or a suction adapter, such as the fluidic connector 710 and the suction adapter 5500 described herein, can be positioned over the one or more openings to deliver negative pressure to the wound and/or collect wound exudate from the wound through the one or more openings and the outlet 8440.

The connector 8400 may be constructed from similar materials with the spacer sections 8600. For example, the spacer sections 8600 can be formed of a porous material. The connector 8400 preferably ensures that an open-air channel can be maintained to communicate negative pressure over the wound area. The connector 8400 may remain open under the typical pressures that will be applied during negative pressure wound therapy as described above, such that the whole wound site sees an equalized negative pressure. The connector 8400 may be formed of a material having a three-dimensional structure. For example, a knitted or woven spacer fabric (for example Baltex 7970 weft knitted polyester, a knitted polyester 3D fabric, Baltex 7970®, or Gehring 879®) or a non-woven fabric (e.g., Glatfelter Vizorb® 3055 MBAL90, Daltex® REPEL, and/or a sterilisable thermally bonded nonwoven viscose and polypropylene non-woven fabric such as Freudenberg M1556N or Vilene) could be used. Suitable materials may also include terry-woven or loop-pile materials. The fibers may not necessarily be woven, and can include felted and flocked (including materials such as Flotex®) fibrous materials. The three-dimensional material can comprise a 3D spacer fabric material similar to the material described in International Publication WO 2013/175306 A2, and International Publication WO2014/020440, the disclosures of which are incorporated by reference in their entireties.

The connector 8400 can comprise of any of the materials and/or additional layers described above for the spacer sections 8600. Further details regarding the materials and dressings of this embodiment may be found in International Application PCT/EP2020/078376 ("App. '376") a filed on Oct. 9, 2020 and International Application PCT/EP2021/058696 ("App. '696") filed on Apr. 1, 2021, the disclosures of which are incorporated by reference in their entireties including, but not limited to, the description accompanying FIGS. 12A-12B of App. '376, and FIGS. 13A-13B of App. '696. For example, the materials described for the transmission layer 1340, 1440 as shown in FIGS. 12A and 13A can be interchanged with the connector 8400.

Figure 11:
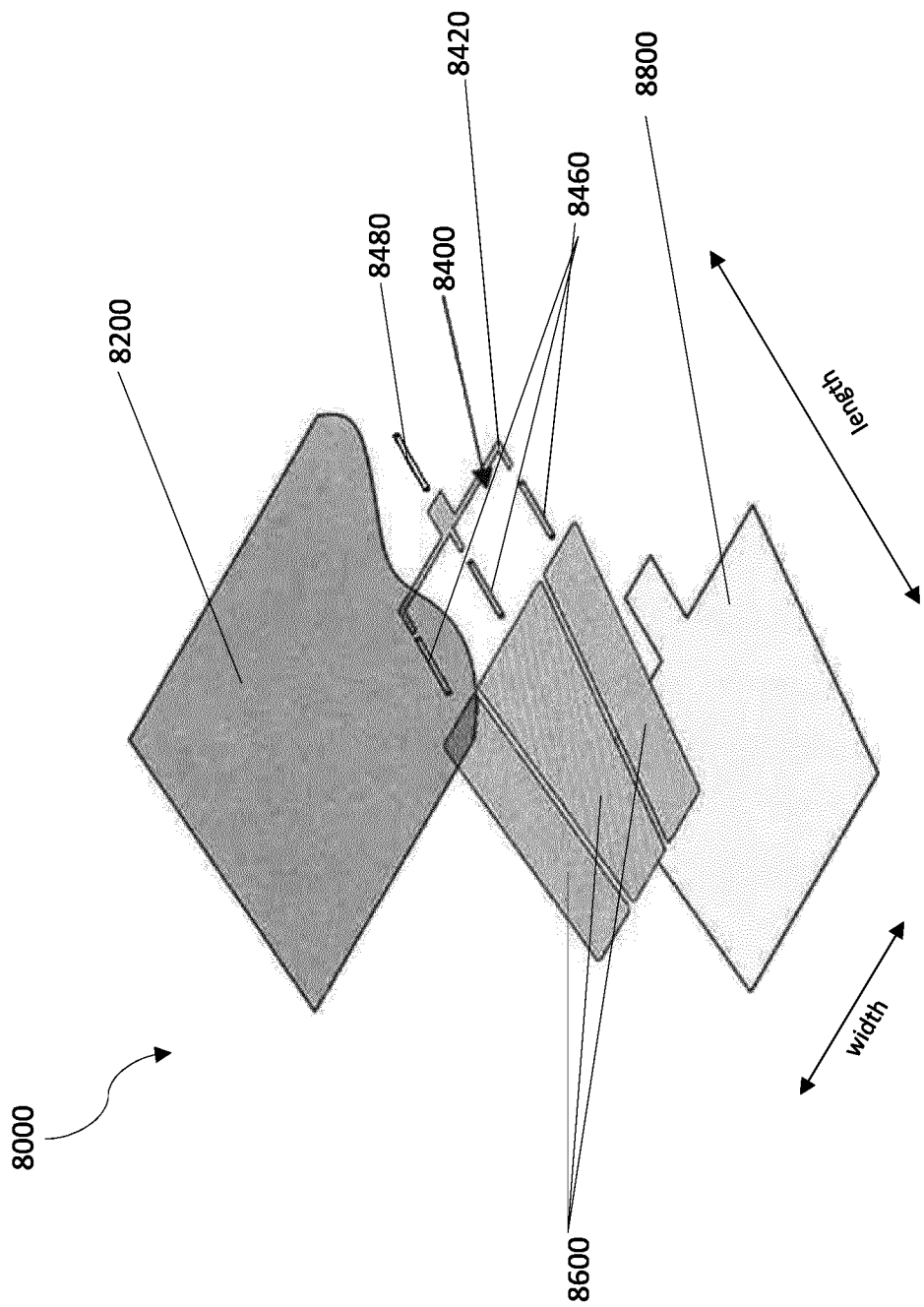
FIG. 11 illustrates an exploded view of a wound dressing according to an embodiment.

In some embodiments, the connector 8400 may include one or more tubes to facilitate fluidic coupling between the connector 8400 and the spacer sections 8600. FIG. 11 illustrates the wound dressing 8000 having a plurality of tubes 8460 connecting the spacer sections 8600 and the inlet 8420. In some embodiments, the tubes 8460 may be at least partially embedded within the material of the spacer sections 8600 and/or the connector 8400. In the illustrated embodiment, the wound dressing 8000 further includes a tube 8480 to be coupled directly with a source of negative pressure, or otherwise fluidically coupled with the source of negative pressure, for example via a conduit. As described herein, the cover layer 8200 and the wound contact layer 8800 may be sealed around the tube 8480 to form a fluid-tight seal. In some embodiments, the tube 8480 may be at least partially embedded within the connector 8400.

As discussed herein, the wound dressing 8000 may be wrapped around the circumferential surface, such that the width of the wound dressing 8000 extends around the circumferential surface. When the wound dressing 8000 is applied around the circumferential surface, the width of the spacer sections 8600 may extend along a portion of the circumference of the circumferential surface, and the length of the spacer sections 8600 may extend along a length of the circumferential surface, approximately perpendicular to the circumference. In some embodiments, the gap regions 8620 are positioned between the spacer sections 8600 as shown in FIGS. 8-9, such that the gap regions 8620 prevent the spacer section 8600 from extending a full circumference of the circumferential surface.

Figure 12:
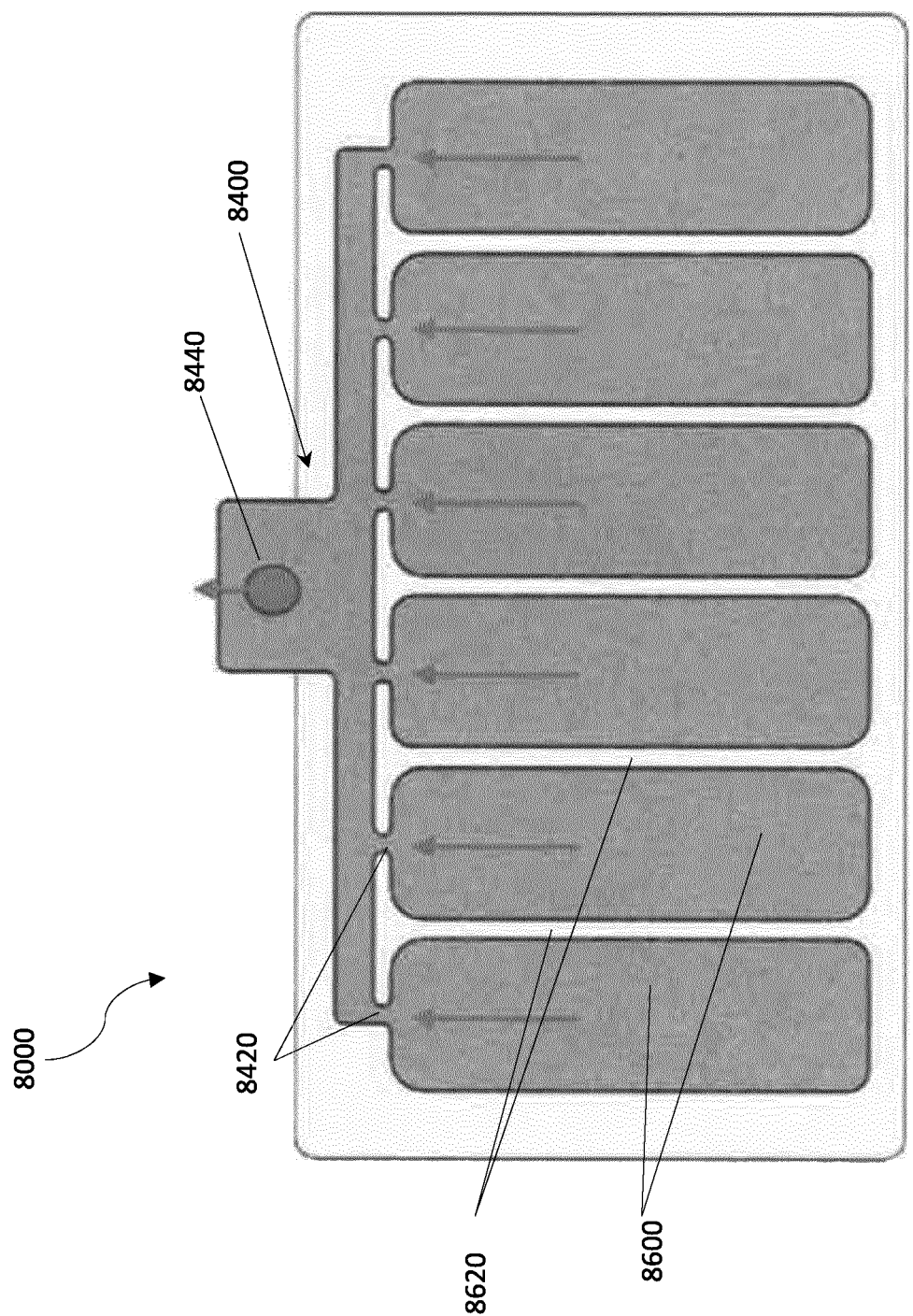
FIG. 12 illustrates a schematic view of fluid flow at an embodiment of a wound dressing.

After the wound dressing 8000 is applied to the circumferential surface, negative pressure may be applied to the wound dressing 8000. FIG. 12 illustrates the flow of fluid when negative pressure is applied to the wound dressing 8000 through the connector 8400. When the source of negative pressure is connected to the outlet 8440 of the wound dressing 8000, the negative pressure can be delivered to the connector 8400 via the outlet 8440, and the negative pressure can be distributed to the wound through the plurality of spacer sections 8600. While the negative pressure is distributed, wound exudate or wound fluid from the wound can be horizontally and/or vertically wicked by the spacer sections 8600 from the wound toward the connector 8400, such that wound exudate or wound fluid can be removed from the wound dressing 8000 through the outlet 8440. In some embodiments, the wound dressing 8000 can manage wound exudate for more than 12 hours, more than 24 hours, or more than 48 hours with a NPWT system. In some embodiments, negative pressure may be only applied to the surface below the spacer sections 8600, and/or may not be applied at the gap regions 8620 between the spacer sections 8600, where the cover layer 8200 and the wound contact layer 8800 are sealed together.

Figure 13:
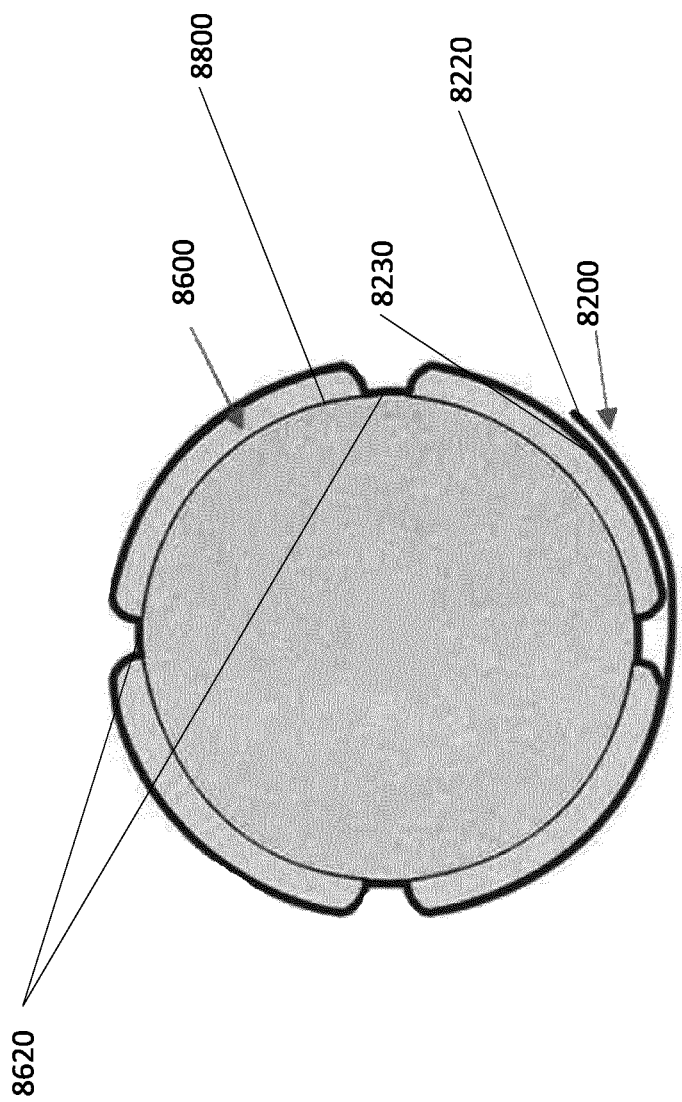
FIG. 13 illustrates a cross-sectional view of an embodiment of a wound dressing applied around a circumferential surface.

FIG. 13 illustrates a cross-sectional view of the wound dressing 8000 applied on a circumferential surface, such as a limb. As discussed herein, the wound dressing 8000 may be wrapped around the circumferential surface, such that the width of the wound dressing 8000 extends around the circumferential surface. In some embodiments, the wound dressing 8000 may have a width same or substantially same with the circumference of the surface, such that the wound dressing 8000 can go around 360° or substantially 360° of the circumferential surface. In some embodiments, the extension 8200 can extend beyond the width of the wound dressing 8000 and can be overlapped with the attachment portion 8230 of the cover layer 8000 to facilitate seal around the surface, as described elsewhere herein. In some embodiments, the wound dressing 8000 may be applied to a limb, such that the connector 8400 is closer to a torso of a patient than an extremity. In some embodiments, the wound dressing 8000 may be applied to a leg, such that the connector 8400 is closer to the extremity than the torso.

As discussed elsewhere herein, the wound dressing 8000 may be used with components of different TNP systems or apparatus. For example, the wound dressing 8000 may be directly or fluidically connected to a source of negative pressure sources, for example using a port, a fluidic connector or a suction adapter, such as the fluidic connector 710 and the suction adapter 5500 described herein. When negative pressure is provided to the wound dressing 8000, negative pressure is delivered at the regions below the plurality of spacer sections 8600 and may pressurize the regions. On the other hand, negative pressure would not be delivered at regions below the gap regions 8620, thus there may be no pressurizing effect of the wound dressing 8000 at the gap regions 8620. Accordingly, the wound dressing 8000 may not deliver the pressure around a full 360° around the circumferential surface, such as a limb, thereby allowing circulation to the extremities. If excessive pressure around a full 360° around the circumferential surface, circulation to the extremities may be negatively affected. Further, unlike the compression bandaging, the compression can be delivered gradually with the control of the TNP systems or apparatus, and the isolated spacer sections 8600 enables delivery of the compression to particular zones. Further, the wound dressing 8000 may be softer at the gap regions 8620 than other areas with the spacer sections 8600, therefore providing comfort and more degrees of freedom to a patient, which may be preferable to a patient who cannot comfortably use the compression bandage dressings due to low pain tolerance. Further, negative pressure from TNP systems or apparatuses can be controlled or adjusted, such that negative pressure applied to the surface can be gradually increased.

Figure 14:
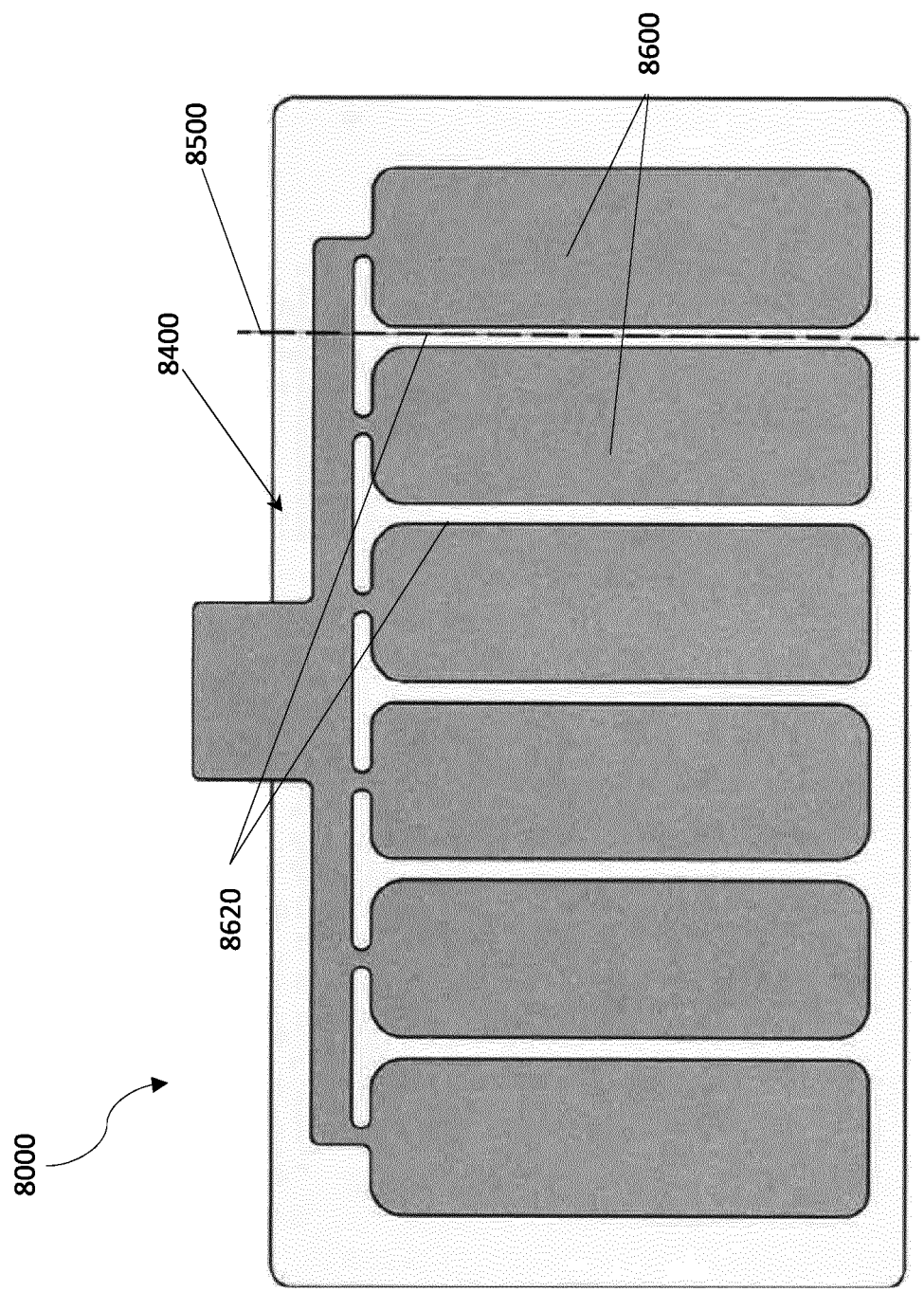
FIG. 14 illustrates a schematic view of trimming an embodiment of a wound dressing.

In some embodiments, the size (e.g. width) of the wound dressing 8000 can be adjusted by a user or a clinician before application to the circumferential surface, such that the wound dressing 8000 conforms to the circumference, size or shape of the circumferential surface such as a limb of a patient. In some embodiments, the wound dressing 8000 may be trimmed at or across one or more locations. For example, the dressing 8000 may be trimmed at or across the gap region 8620. FIG. 14 illustrates trimming of the wound dressing 8000 according to one embodiment. As illustrated in FIG. 14, the wound dressing 8000 may be trimmed along a trim line 8500 along the gap region 8620 and across the connector 8400. Although the dressing 8000 may be trimmed at any portion, trimming the dressing along the line 8500 across the connector 8400, for example perpendicular to the width of the dressing 8000, enables easier sealing as a narrower cross sectional area is exposed, and thus less area requires sealing after trimming. It will be appreciated that the dressing may be trimmed at locations other than the illustrated trim line 8500, which is included for illustrative purposes only, for example at a diagonal or curved trim line. In some embodiments, layers of the wound dressing 8000 may be pre-scored for sizing. In some embodiments, the wound dressing 8000 may include a printed or indented pattern on some or all of the layers to indicate possible trim lines.

After trimming, the wound dressing 8000 may be sealed by an adhesive strip, a piece of a sealing drape, by another dressing, or by a sealant. It will be appreciated that any other adhesive method or mechanism may be used to seal the dressing. For example, a sealant may be applied with a tool such as a syringe around the trimmed area in order to reseal the chamber of the dressing or to seal the dressing to a patient. Some embodiments of the dressing 8000 may be self-sealing.

Figure 15:
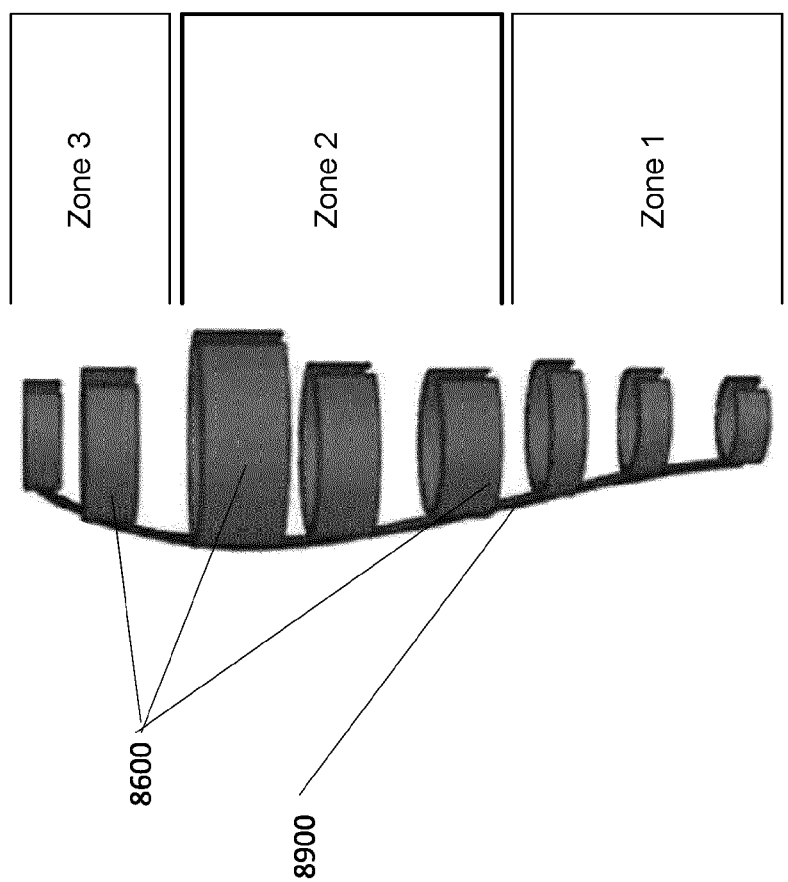
FIG. 15 illustrates a component of an embodiment of a wound dressing according to one embodiment.

In some embodiments, the plurality of spacer sections 8600 can be positioned such that there are multiple spacer sections 8600 along the length of the wound dressing 8000 while each spacer sections extends along the width of the wound dressing 8000, as shown in FIG. 15. In the illustrated embodiment, each of the spacer sections 8600 may extend horizontally along circumference of the circumferential surface, such as a limb, wrapping around the surface. In the illustrated embodiment, a vertical connector 8900 extending vertically along the length of the circumferential surface, can fluidically connect the spacer sections 8600. By arranging spacer sections 8600 horizontally as shown in FIG. 15, negative pressure may be provided differently at different zone of treatment (e.g. Zones 1, 2, 3 shown in FIG. 15).

Terminology

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above,"

"below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein. Certain embodiments of the disclosure are encompassed in the claim set listed below or presented in the future.

What is claimed is:

1. A negative pressure wound therapy dressing configured for treating a circumferential surface, comprising:
   a cover layer;
   a wound contact layer;
   a plurality of spacer sections positioned between the cover layer and the wound contact layer, each spacer section separated from another spacer section by a gap region therebetween, wherein the cover layer and the wound contact layer are configured to be sealed together at individual gap regions;
   a port configured to be connected to a source of negative pressure;
   a connector configured to fluidically connect each of the plurality of spacer sections with the port; and
   a trim line along at least one gap region and across the connector.

2. The negative pressure wound therapy dressing of claim 1, wherein the connector comprises a plurality of inlets connected to the plurality of spacer sections and an outlet connected to the port.

3. The negative pressure wound therapy dressing of claim 1, wherein the connector comprises a spacer fabric material.

4. The negative pressure wound therapy dressing of claim 1, wherein each of the spacer sections comprise a distal end, a proximal end, a length extending from the distal end to the proximal end, and a width perpendicular to the length.

5. The negative pressure wound therapy dressing of claim 4, wherein the connector is connected to the proximal end of a spacer section.

6. The negative pressure wound therapy dressing of claim 4, wherein the length is greater than the width.

7. The negative pressure wound therapy dressing of claim 1, wherein each of the spacer sections is fluidically isolated from the other spacer sections except for at the connector.

8. The negative pressure wound therapy dressing of claim 1, further comprising one or more tubes connecting the plurality of spacer sections and the connector.

9. The negative pressure wound therapy dressing of claim 1, wherein the cover layer comprises one or more openings and the port is positioned above the one or more openings.

10. The negative pressure wound therapy dressing of claim 1, wherein the cover layer comprises an extension portion at one end of the cover layer, wherein the extension portion can be overlapped over another regions of the cover layer when the dressing is applied to a wound.

11. A method of treating a circumferential wound comprising:
    providing a wound dressing comprising:
       a cover layer,
       a wound contact layer,
       a plurality of spacer sections positioned between the cover layer and the wound contact layer, each spacer section separated from another spacer section by a gap region therebetween, wherein the cover layer and the wound contact layer are configured to be sealed together at individual gap regions,
       a port configured to be connected to a source of negative pressure, and
       a connector configured to fluidically connect each of the plurality of sections with the port;
    applying the wound dressing around the circumferential wound; and
    trimming a portion of the wound dressing along a trim line along at least one gap region and across the connector.

12. The method of claim 11, wherein applying the wound dressing around the circumferential wound comprises wrapping the wound dressing around the circumferential wound such that an end of the cover layer overlaps with another end of the cover layer.

13. The method of claim 12, wherein the cover layer comprises an extension portion at one end of the cover layer, wherein the extension portion can be overlapped over another regions of the cover layer.

14. The method of claim 11, further comprising applying negative pressure to the circumferential wound through the port.

15. The method of claim 11, wherein the connector comprises a plurality of inlets connected to the plurality of spacer sections and an outlet connected to the port.

16. The method of claim 11, wherein the connector comprises a spacer fabric material.

17. The method of claim 11, wherein each of the spacer sections comprise a distal end, a proximal end, a length extending from the distal end to the proximal end, and a width perpendicular to the length, wherein applying the wound dressing around the circumferential wound comprises positioning the length of the spacer sections along the length of the circumferential wound.

\* \* \* \* \*